United States Patent
Guan et al.

[11] Patent Number: 6,149,882
[45] Date of Patent: Nov. 21, 2000

[54] PARALLEL FIXED BED REACTOR AND FLUID CONTACTING APPARATUS

[75] Inventors: Shenheng Guan, San Jose; Lynn Van Erden, Livermore; Robert C. Haushalter, Los Gatos; Xiao Ping Zhou, Sunnyvale; Xuejun Jason Wang, Fremont; Ravi Srinivasan, Mountain View, all of Calif.

[73] Assignee: Symyx Technologies, Inc., Santa Clara, Calif.

[21] Appl. No.: 09/093,870

[22] Filed: Jun. 9, 1998

[51] Int. Cl.[7] .................................................... B01J 35/02
[52] U.S. Cl. .......................... 422/211; 422/81; 422/83; 422/63; 422/89; 422/131; 422/213; 436/43; 436/161; 436/174; 436/180
[58] Field of Search .................... 422/83, 81, 63, 422/131, 89, 211, 213; 436/43, 174, 180, 161

[56] References Cited

U.S. PATENT DOCUMENTS

| | | | |
|---|---|---|---|
| 3,431,077 | 3/1969 | Danforth | 23/253 |
| 3,760,831 | 9/1973 | Colvin | 137/117 |
| 4,099,923 | 7/1978 | Milberger | 23/254 R |
| 4,705,669 | 11/1987 | Tsuji et al. | 422/93 |
| 4,895,706 | 1/1990 | Root et al. | 422/102 |
| 4,996,387 | 2/1991 | Gerhold et al. | 585/654 |
| 5,035,866 | 7/1991 | Wannlund | 422/102 |
| 5,246,665 | 9/1993 | Tyranski et al. | 422/64 |
| 5,304,354 | 4/1994 | Finley et al. | 422/196 |
| 5,324,483 | 6/1994 | Cody et al. | 422/131 |
| 5,340,475 | 8/1994 | Cortes et al. | 210/198.2 |
| 5,467,635 | 11/1995 | Nakagawa et al. | 73/23.35 |
| 5,587,128 | 12/1996 | Wilding et al. | 422/50 |
| 5,710,381 | 1/1998 | Atwood et al. | 73/864.91 |
| 5,753,185 | 5/1998 | Mathews et al. | 422/94 |
| 5,922,286 | 7/1999 | Girard et al. | 422/83 |

FOREIGN PATENT DOCUMENTS

| | | | |
|---|---|---|---|
| 0 803 288 A2 | 12/1997 | European Pat. Off. | B01L 3/00 |
| 0 870 541 A2 | 10/1998 | European Pat. Off. | B01J 19/00 |
| WO 97/32208 | 9/1997 | WIPO | G01N 31/10 |
| WO 98/03521 | 1/1998 | WIPO | C07F 19/00 |
| WO 98/07026 | 2/1998 | WIPO | G01N 31/10 |
| WO 98/52691 | 11/1998 | WIPO | B01L 3/00 |

OTHER PUBLICATIONS

J.T. Richarson et al., Characterization and Deactivation of NiO—$ThO_2$ Catalysts, Applied Catalysis, 48, pp. 159–176, (1989).

Unit Instruments, Basics of Thermal Mass Flow Control, Oct. 17, 1990.

Martin et al., 1993, Analytica Chimica Acta, 281: 557–568 "Integrated enzyme reactor/detector for the determination of multiple substrates by image analysis".

Martinec et al., 1987, Chemical Abstracts 107:p. 122 "Apparatus for testing the service life of industrial heterogeneous catalysts".

Moates et al., 1996, Ind. Eng. Chem. Res. 35: 4801–4803 "Infrared Thermographic Screening of Combinatorial Libraries of Heterogeneous Catalysts".

*Primary Examiner*—Long V. Le
*Assistant Examiner*—Kath Bex

[57] ABSTRACT

The present invention discloses an apparatus and method for rapid analysis of members of a combinatorial library. The apparatus includes a plurality of vessels for containing individual library members and a fluid handling system that apportions a test fluid about equally between each of the vessels. This allows for simultaneous screening of library members by detecting changes in test fluid following contact with individual library members. Fluid flow through each of the vessels is controlled using passive flow restrictors or active flow controllers to ensure that each library member contacts approximately the same amount of test fluid per unit time. The disclosed apparatus is especially useful for screening library members based on their ability to catalyze the conversion of fluid reactants.

50 Claims, 11 Drawing Sheets

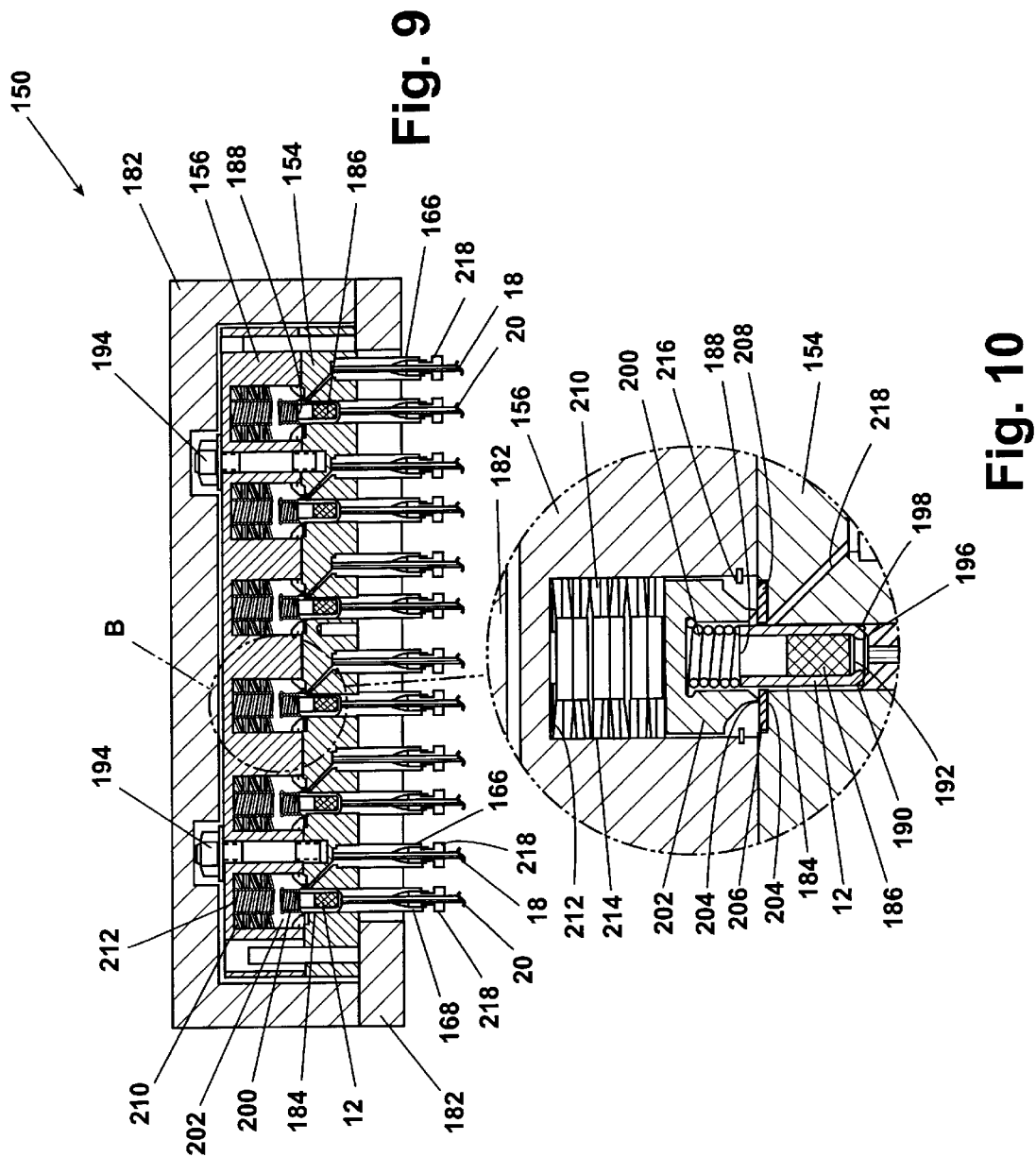

PARALLEL FIXED BED REACTOR AND FLUID CONTACTING APPARATUS

BACKGROUND

1. Technical Field

The present invention relates generally to systems for high speed analysis of combinatorial libraries by contacting a plurality of library members simultaneously with a test fluid, and more particularly, to an apparatus and method for screening library members based on each member's ability to catalyze the conversion of fluid reactants.

2. Discussion

Combinatorial chemistry refers to methods for creating chemical libraries—vast collections of compounds of varying properties—that are tested or screened in order to identify a subset of promising compounds. Depending on how they are made, libraries may consist of substances free in solution, bound to solid supports, or arrayed on a solid surface.

The advent of combinatorial chemistry promises to change the discovery and development of new and useful materials. For example, workers in the pharmaceutical industry have successfully used such techniques to dramatically increase the speed of drug discovery. Material scientists have employed combinatorial methods to develop novel high temperature superconductors, magnetoresistive materials, and phosphors. More recently, scientists have applied combinatorial methods to catalyst development. See, for example, copending U.S. patent application Ser. No. 08/327,513 "The Combinatorial Synthesis of Novel Materials" (published as WO 96/11878) and copending U.S. patent application Ser. No. 08/898,715 "Combinatorial Synthesis and Analysis of Organometallic Compounds and Catalysts" (published as WO 98/03521), which are both herein incorporated by reference.

Once a researcher creates a combinatorial library, he or she must screen tens, hundreds or even thousands of compounds. Existing analytical methods and devices, which were originally designed to characterize a relatively small number of compounds, are often ill-suited to screen combinatorial libraries. This is true in catalyst research where, up until now, there has been little need to rapidly test or characterize large numbers of compounds at one time.

In traditional catalyst development, for example, researchers synthesize relatively large amounts of a candidate compound. They then test the compound to determine whether it warrants further study. For solid phase catalysts, this initial testing involves confining the compound in a pressure vessel, and then contacting the compound with one or more fluid phase reactants at a particular temperature, pressure and flow rate. If the compound produces some minimal level of reactant conversion to a desired product, the compound undergoes more thorough characterization in a later step.

Because synthesis consumes a large fraction of the development cycle in traditional catalyst studies, researchers have expended little effort to speed up the screening step. Thus, although test reactors have been steadily improved over the years, most were simply automated to reduce labor needed to operate them. Even automated catalyst screening devices comprised of multiple reaction vessels were operated sequentially, so that the reaction time for a group of candidate compounds was about the same as could be achieved with a single-vessel reactor.

Conventional catalyst screening devices have other problems as well. For example, traditional experimental fixed bed reactors require relatively large catalyst samples. This makes them impractical for screening combinatorial libraries. With combinatorial methods, one obtains increased chemical diversity at the expense of sample size. Individual library members may therefore consist of no more than a milligram (mg) or so of material. In contrast, conventional fixed bed reactors typically require 10 g or more of each candidate compound.

The present invention overcomes, or at least minimizes, one or more of the problems set forth above.

SUMMARY OF THE INVENTION

In accordance with one aspect of the present invention, there is provided an apparatus for screening members of a combinatorial library by contacting library members with a test fluid. The apparatus includes a plurality of vessels for receiving the library members, a detector for analyzing changes in test fluid following contact with library members, and a fluid handling system that is designed to apportion test fluid about equally between each of the vessels. The fluid handling system comprises an entrance control volume and an exit control volume that are in fluid communication with the inlets and the outlets of the vessels, respectively. A plurality of flow restrictors provide fluid communication between the vessels and either the entrance control volume or the exit control volume. During screening, a higher pressure is maintained in the entrance control volume than in the exit control volume so that test fluid flows from the entrance control volume than in the exit control volume through the vessels. The test fluid is split about equally between each vessel because the resistance to fluid flow is greater in the flow restrictors, varies little between individual flow restrictors, and is much larger than resistance to fluid flow in the vessels and other components of the fluid handling system.

In accordance with a second aspect of the present invention, there is provided an apparatus for screening members of a combinatorial library by simultaneously contacting library members with a test fluid. The apparatus includes a plurality of vessels for receiving the library members, a detector for analyzing changes in test fluid following contact with library members, and a fluid handling system that is designed to apportion test fluid about equally between each of the vessels. The fluid handling system comprises an entrance control volume, and a plurality of flow restrictors that provide fluid communication between the vessel inlets and the entrance control volume. The fluid handling system also includes a plurality of outlet conduits and a selection valve, the outlet conduits providing fluid communication between the vessel outlets and the selection valve. The selection valve is adapted to divert fluid from a selected vessel to a sample bypass while allowing fluid from non-selected vessels to flow to an exit control volume via a common exhaust port. A return line vents most of the test fluid in the sample bypass into the exit control volume, through a small fraction is sent to the detector for analysis. Fluid in the sample bypass is split between the exit control volume and detector using a sampling valve, which provides selective fluid communication between the sample bypass and the exit control volume, and between the sample bypass and the detector. During screening, a higher pressure is maintained in the entrance control volume than in the exit control volume so that test fluid flows from the entrance control volume to the exit control volume through the vessels. The test fluid is split about equally between each vessel because the resistance to fluid flow is greatest in the flow restrictors, varies little between individual flow restrictors, and is much larger than resistance to fluid flow in the other components of the fluid handling system.

In accordance with a third aspect of the present invention, there is provided a reactor for evaluating catalytic performance of members of a combinatorial library by contacting library members with a reactive fluid. The apparatus includes a plurality of vessels for receiving the library members, and a fluid handling system that is designed to apportion the reactive fluid about equally between each of the vessels. The fluid handling system comprises an entrance control volume and exit control volume that are in fluid communication with the inlets and outlets of the vessels, respectively. A plurality of flow restrictors provide fluid communication between the vessels and either the entrance control volume or the exit control volume. During screening, a higher pressure is maintained in the entrance control volume than in the exit control volume so that test fluid flows from the entrance control volume to the exit volume through the vessels. The reactive fluid is split about equally between each vessel because the resistance to fluid flow is greatest in the flow restrictors, varies little between individual flow restrictors, and is much larger than resistance to fluid flow elsewhere in the fluid handling system.

In accordance with a fourth aspect of the present invention, there is provided a method of screening members of a combinatorial library comprising the steps of confining about equal amounts of a group of library members in a plurality of vessels, contacting each of the confined library members with a test fluid by flowing the test fluid through each of the vessels, and detecting changes in the test fluid following contact with each of the confined library members. Changes in the test fluid are then related to a property of interest, such as catalytic activity and selectivity. The contacting step and the detecting step are carried out for at least two of the confined library members simultaneously, and the amount of test fluid flowing through each of the vessels per unit time is about the same.

The detecting step can include measuring changes in the composition of the test fluid. The total time required to screen at least six library members is less than about six minutes, or in some embodiments, less than about three minutes. The total time required to screen at least forty-eight library members is less than about forty-eight minutes, or in some embodiments, less than about twenty-four minutes.

BRIEF DESCRIPTION OF THE DRAWINGS

FIG. 9 shows a cross-sectional view of one embodiment of a vessel assembly.

FIG. 10 provides a close-up, cross sectional view of the wells and vessels.

DETAILED DESCRIPTION OF THE PREFERRED EMBODIMENTS

Overview of Screening Apparatus and Method

The present invention provides an apparatus and method for rapidly screening members of a combinatorial library. High throughput screening is achieved by contacting a group of library members with about equal amounts of a test fluid. Screening can be simultaneous for two or more library members or carried out in a rapid serial manner. Changes in the test fluid resulting from contact with library members are used to identify members worthy of further study. In the following disclosure, the term "fluid" refers to any substance that will deform continuously under the action of a shear force, including both gases and liquids.

The apparatus and method can be used to screen library members based on any property that can be discerned by detecting or measuring changes in a test fluid following contact with a library member. Thus, for example, library members can be screened for catalytic activity by contacting each library member with a reactive fluid. The best performing library members are those that result in the highest concentration of a desired reaction product in the test fluid following contact.

The disclosed invention is not limited to screening catalysts, but can be used for rapid screening of many different types of materials. For example, the method and apparatus can be used to screen library members based on their ability to filter out or adsorb a specific gas species. The concentration of that gas species in a fluid stream following contact with a particular library member is inversely proportional to the particular material's performance. Similarly, polymeric materials synthesized using combinatorial methods can be screened for thermal stability by measuring the concentration of gaseous decomposition products in an inert fluid stream in contact with heated library members. The amount of decomposition product evolved by a particular polymeric material is a measure of that material's thermal stability.

Figure 1:
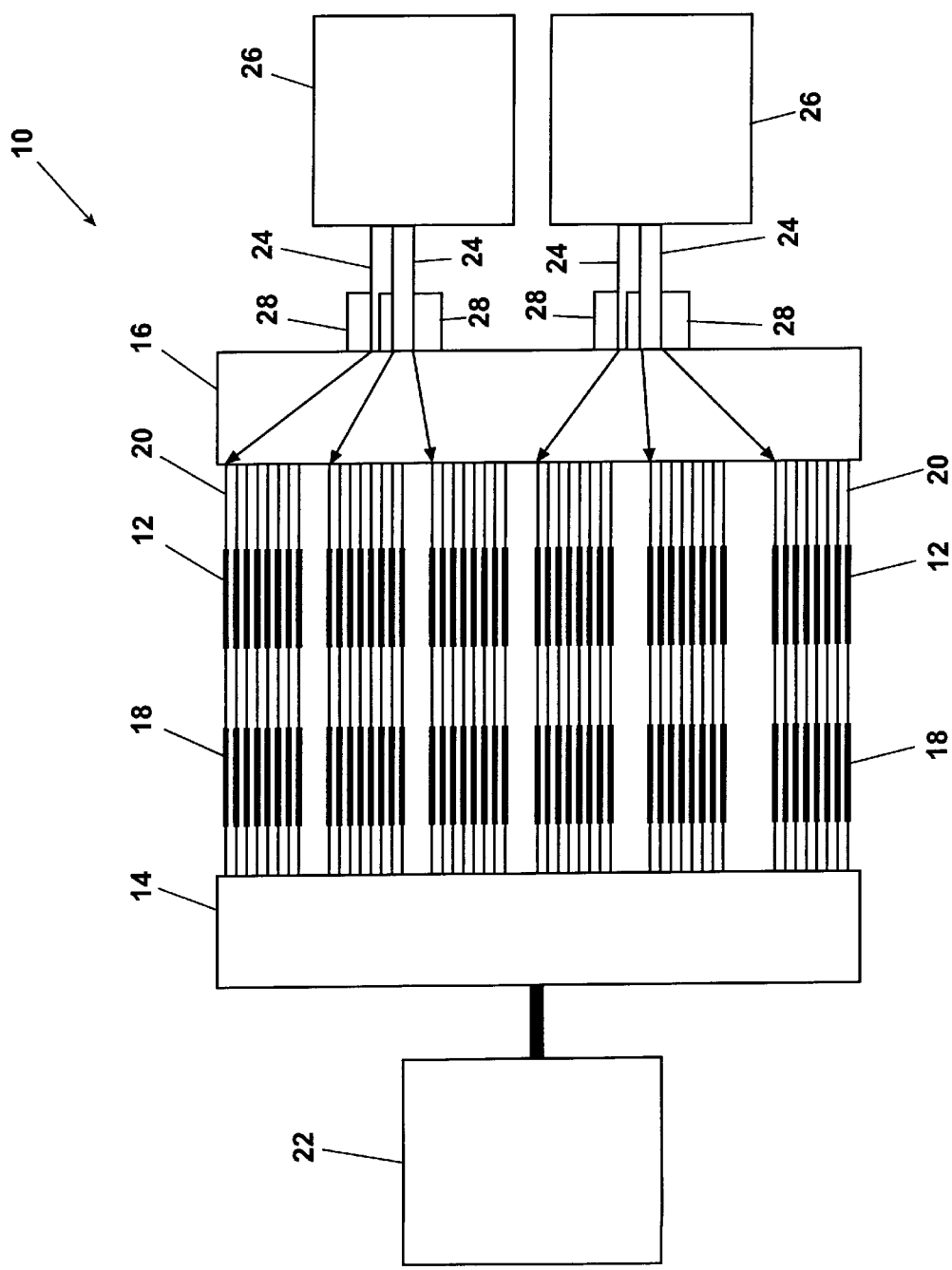
FIG. 1 is a schematic drawing of an apparatus for rapidly screening members of a combinatorial library.

FIG. 1 schematically shows one embodiment of an apparatus for rapidly screening members of a combinatorial library. The screening apparatus 10 is comprised of a plurality of vessels 12 for receiving members of the combinatorial library. Each of the vessels 12 is in fluid communication with an entrance control volume 14 and exit control volume 16 through flow restrictors 18 and outlet conduits 20, respectively. In another embodiment, the vessels are in direct fluid contact with the entrance control volume, and the flow restrictors replace the outlet conduits.

Members of a combinatorial library are screened by simultaneously contacting a subset of library members with nearly equal amounts of test fluid. The test fluid is prepared in a fluid mixing unit 22, which is in fluid communication with the entrance control volume 14. During screening, a higher pressure is maintained in the entrance control volume 14 than in the exit control volume 16. As a result, the test fluid flows from the entrance control volume 14, through the flow restrictors 18 and through each of the vessels 12.

The flow restrictors 18 are designed to exert the greatest resistance to fluid flow along flow paths between the entrance 14 and exit 16 control volumes. The flow restrictors 18 can be any structure that hinders fluid flow including capillary tubes, micromachined channels, and pin hole obstructions within a conduit.

Because fluid flow resistance—pressure drop—is greatest in the flow restrictors 18 and varies little among individual restrictors 18, the test fluid is apportioned about equally between each of the vessels 12. This is important because the extent of change in the test fluid following contact with a library member depends on, among other things, the time a given amount of test fluid contacts the library member.

Typically, solid library members are supplied to each of the vessels 12 in the form of a fixed bed: the library members are either supported on solid particles or are themselves granular or porous solids. In such cases, the test fluid flows through the interstices in the fixed bed, ensuring intimate contact between the test fluid and the library member. Similarly, liquid library members are confined within the vessels 12 by capillary forces, and fluid contact occurs by bubbling test gas through the vessels 12. Following fluid/solid or fluid/liquid contacting, the test fluid exits each of the vessels 12 through outlet conduits 20 that convey the test fluid to the exit control volume 16.

Most vessel effluent dumps directly into the exit control volume 16. However, test fluid selected vessels 12 is routed from the outlet conduits 20 through a sample bypass 24 to a detector 26, which measures changes in the test fluid resulting from contact with a library member. Almost all of the fluid in the sample bypass 24 is returned to the exit control volume 16 through a return line 28; only a small fraction is actually sent to the detector 26 for analysis. Although the screening apparatus 10 depicted in FIG. 1 has two detectors 26, and each detector 26 can analyze vessel effluent from three vessels 12 simultaneously, the number of detectors 26 can be varied. Furthermore, the ability of each detector 26 to analyze test fluid from more than one of the vessels 12 simultaneously will depend on the type of detector 26. A useful detector 26 for screening catalysts includes a gas chromatograpgh (GC), which can measure concentration of a desired reaction product in vessel effluent. Other useful detectors include mass spectrometers, as well as ultraviolet, visible, and infrared spectrometers.

Fluid Handling System

Figure 2:
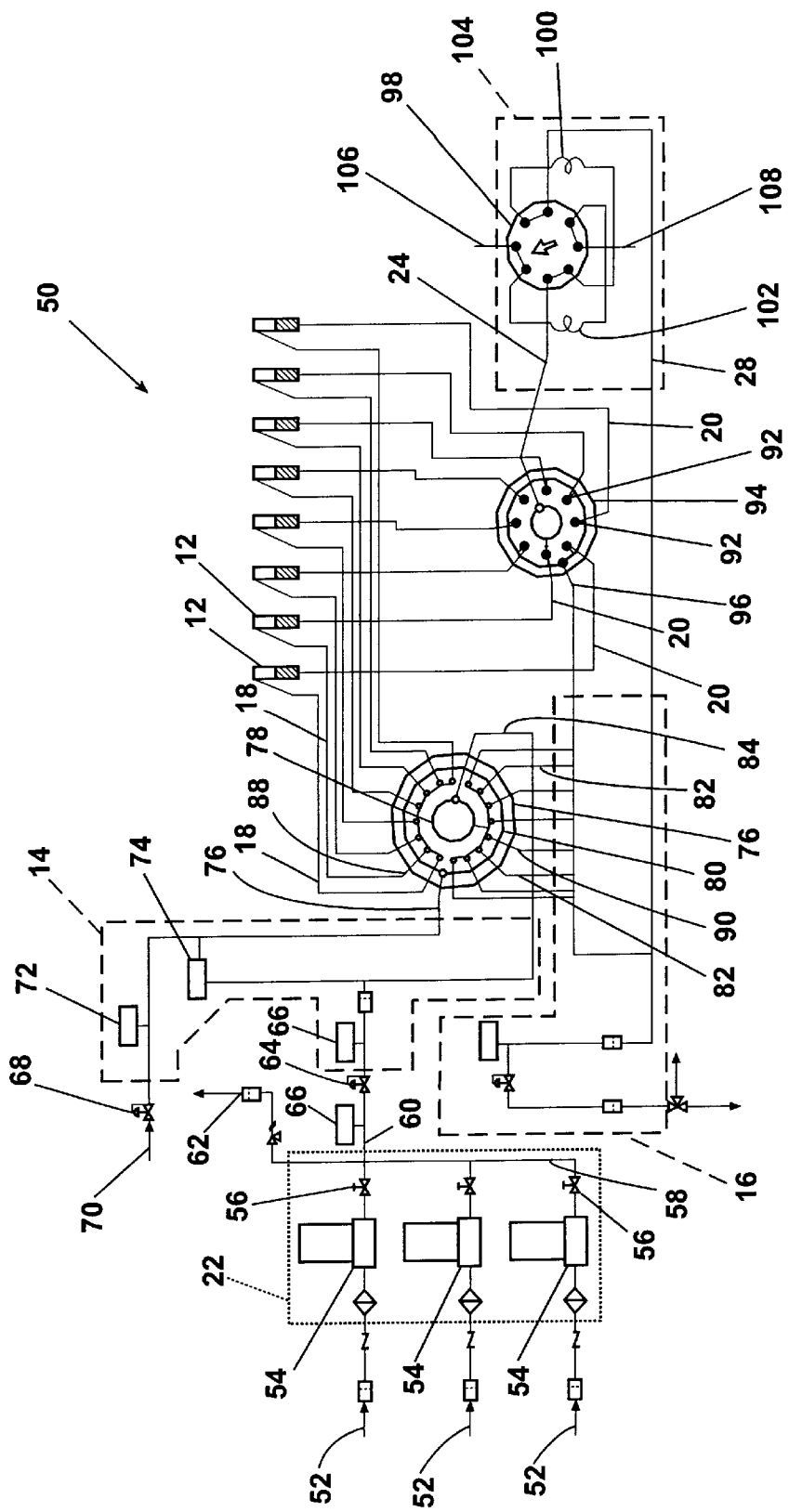
FIG. 2 is a schematic drawing of a fluid handling system of the screening apparatus.
Figure 3:
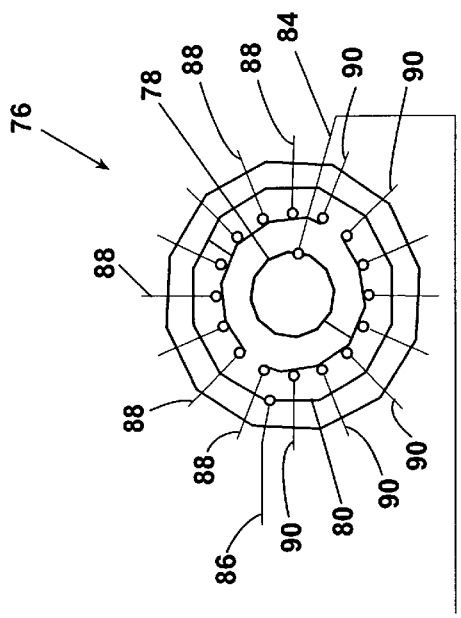
FIG. 3 through FIG. 6 show four different settings of a first valve portion and a second valve portion of a fluid distribution valve.
Figure 4:
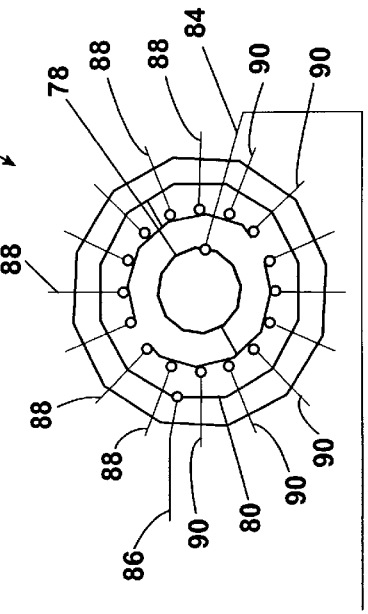

The fluid mixing unit 22, the entrance control volume 14, and the exit control volume 16 comprise a fluid handling system. Further details of one embodiment of the fluid handling system 50 are shown in FIG. 2. For clarity, FIG. 2 illustrates a fluid handling system 50 suitable for screening potential catalysts. However, the system can be used to screen library members based on any criteria discernible by detecting changes in a test fluid following contact with library members.

The test fluid is prepared in the fluid mixing unit 22, which comprises test fluid sources 52 in fluid connection with conventional mass flow controllers 54. The mass flow controllers 54 adjust the amount of each test fluid constituent. Isolation valves 56 allow each fluid source to be taken off line. Fluids from individual sources 52 flow through the mass flow controllers 54 and are combined in a manifold 58. From there, the test fluid flows into the entrance control volume 14 through a feed line 60. If necessary, the test fluid can vent through an exhaust port 62.

The entrance control volume 14 provides the vessels 12 with test fluid at a constant pressure. A feed line control valve 64 adjusts the flow rate of test fluid entering the entrance control volume 14 from the test fluid mixing unit 22. A pair of feed line transducers 66 monitor pressure immediately upstream and downstream of the control valve 64. Both pressure transducers 66 and the control valve 64 communicate with a processor (not shown). Pressure data from the transducers 66 is periodically sent to the processor. Based on these data, the processor transmits a signal to the control valve 64, which adjusts the test fluid flow rate through the feed line 60, and maintains constant test fluid pressure in the entrance control volume 14.

The entrance control volume 14 shown in FIG. 2 optionally provides the vessels 12 with an inert fluid at the same pressure as the test fluid (the use of the inert fluid is discussed below). An inert fluid control valve 68 adjusts the flow rate of inert fluid entering the entrance control volume 14 from an inert fluid source 70. An inert fluid feed line transducer 72 monitors pressure immediately downstream of the control valve 68. The transducer 72 and the control valve 68 communicate with a processor (not shown). Pressure data from the transducer 72 is periodically sent to the processor, which, based on the pressure data, transmits a signal to the control valve 68. In response to the signal, the control valve 68 adjusts the flow rate of the inert fluid entering the entrance control volume 14, thereby maintaining desired pressure. A differential pressure transducer 74, which communicates with both the test fluid and the inert fluid streams within the entrance control volume 14, provides a measure of the pressure difference between the two fluid streams. Ideally, the pressure difference should be negligible.

The properties of some library members may change during exposure to test fluid. For example, a sample may exhibit high catalytic activity during initial contact with a reactive fluid, but a short time later, may show a precipitous decline in activity. Conversely, a sample may show an increase in catalytic activity with elapsed contact time. In such cases, one must ensure that the time from initial contact with the test fluid to detection of changes in the test fluid is about the same for each sample; otherwise, when using a combination of parallel and serial screening, a sample's perceived performance will depend on position within the screening cycle.

The fluid handling system 50 shown in FIG. 2 has an optional fluid distribution valve 76 that ensures that the time interval between initial contact and detection is about the same for each sample. At the beginning of a screening cycle, the distribution valve 76 directs inert fluid into each of the vessels 12 via flow restrictors 18. At pre-selected times, the distribution valve 76 sequentially directs test fluid into each of the vessels. The times at which the detector measure changes in the test fluid from each of the vessels are synchronized with the pre-selected start times.

The fluid distribution valve 76 is comprises of a first valve portion 78 and a second valve portion 80. The first valve portion 78 provides selective fluid communication between the test fluid and the flow restrictors 18, and between the test fluid and a plurality of exhaust conduits 82. The second valve portion 80 provides selective fluid communication between the inert fluid and the flow restrictors 18, and between the inert fluid and exhaust conduits 82. The exhaust conduits 82 have the same fluid resistance as the flow restrictors 18, and channel fluid into the exit control volume 16. Because the resistance to fluid flow is about the same in individual flow restrictors 18 and exhaust conduits 82, both the test fluid and the inert fluid are apportioned about equally among each of the flow restrictors 18 and exhaust conduits 82.

FIG. 3 through FIG. 6 illustrate the operation of one embodiment of the fluid distribution valve 76. Test fluid and inert fluid enter the distribution valve 76 from the entrance control volume through a test fluid port 84 and an inert fluid port 86, respectively. The distribution valve 76 splits the two fluid streams about equally between first outlet ports 88, which channel fluid into the flow restrictors (not shown), and second outlet ports 90, which channel fluid into the exhaust conduits (not shown). Although the distribution valve 76 shown in the figures has sixteen outlet ports divided equally among the first 88 and second 90 outlet ports, the number of outlet ports can vary.

Figure 5:
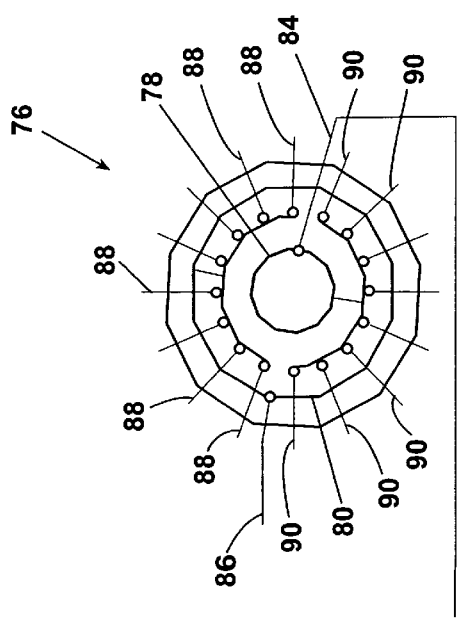
Figure 6:
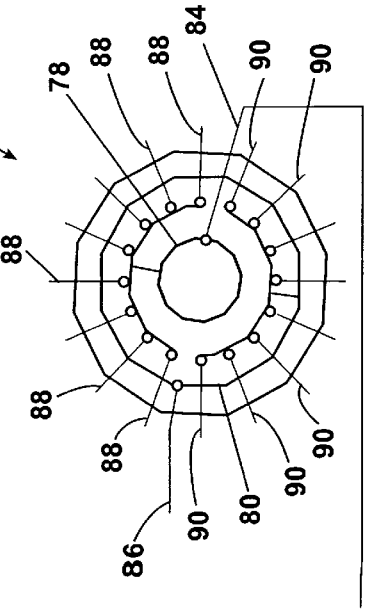

FIG. 3 through FIG. 6 show four different settings of the first valve portion 78 and the second valve portion 80. In a first setting shown in FIG. 3, the first valve portion 78 diverts all of the test fluid through the second outlet port 90, and the second valve portion 80 diverts all of the inert fluid through the first outlet ports 88. In a second setting shown in FIG. 4, the first valve portion 78 and the second valve portion 80 are rotated clockwise so that inert fluid flows through seven of the first outlet ports 88 and one of the second outlet ports 90, and the test fluid flows through seven of the second outlet ports 90, and one of the first outlet ports 88. Further clockwise rotation of the first 78 and second 80 valve portions results in a third setting where, as shown in FIG. 5, inert fluid flows through six of the first outlet ports 88 and two of the second outlet ports 90, and test fluid flows through six of the second outlet ports 90, and two of the first outlet ports 88. Rotation of the first 78 and the second 80 valve portions through one hundred eighty degrees results in a fourth setting shown in FIG. 6, where all of the test fluid flows through the first outlet ports 88, and all of the inert fluid flows through the second outlet ports 90.

Referring again to FIG. 2, test fluid leaves the distribution valve 76 via the first outlet ports 88, flows through the restrictors 18 into the vessels 12 where it contacts individual library members. The test fluid exits the vessels 12 through outlet conduits 20, and eventually vents into the exit control volume 16. Each of the outlet conduits 20 is in fluid connection with one of a plurality of inlet ports 92 of a selective valve 94. The selection valve selectively diverts most of the vessel effluent streams directly into the exit control volume 16 via a common exhaust port 96. However, the selection valve 94 selectively routes fluid from one of the vessels 12 through a sample bypass 24 to a detector (not shown), which measures changes in the test fluid resulting from contact with a library member. Fluid in the sample bypass 24 is returned to the exit control volume 16 through a return line 28. Although the selection valve 94 depicted in FIG. 2 receives fluid from eight vessels 12, the selection valve 94 can be designed to accommodate more or less vessels 12. Moreover, the fluid handling system 50 can comprise more than one selection valve 94, so that fluid from two or more vessels 12 can be analyzed simultaneously using either multiple detectors or a multiple channel detector.

The fluid handling system 50 shown in FIG. 2 uses a sampling valve 98 to send a fixed volume of fluid to the detector without upsetting the volumetric flow rate throughout the rest of the fluid handling system 50. The sampling valve 98 is in fluid communication with a first metering tube 100 and a second metering tube 102, and is adapted to switch between a first flow network 104 and a second flow network (not shown). The first metering tube 100 and the second metering tube 102 have about the same volume.

The first flow network 104 provides a flow path from one of the vessels 12 to the exit control volume 16 through the sample bypass 24, the sampling valve 98, the first metering tube 100, and the return line 28. The first flow network 104 also provides a flow path from a carrier fluid source 106 to a detector inlet port 108 through the sampling valve 98 and the second metering tube 102. In contrast, the second flow network provides a flow path from one of the vessels 12 to the exit control volume 16 through the sample bypass 24, the sampling valve 98, the second metering tube 102, and the return line 28, and provides a flow path from the carrier fluid source 106 to the detector inlet port 108 through the sampling valve 98 and the first metering tube 100.

The sampling valve 98 sends a fixed volume of fluid to the detector by either switching between the first flow network 104 and the second flow network, or by switching between the second flow network and the first flow network 104. For example, while the sampling valve 98 is switched to the first flow network 104, fluid from one of the vessels 12 flows through the first metering tube 100, while carrier fluid flows through the second metering tube 102. After a time, the sampling valve 98 is switched to the second flow network so that the volume of fluid in the first metering tube 100 is swept by the carrier flue through the detector inlet port 108 to the detector. Meanwhile, fluid from another one of the vessels 12 flows through the second metering tube 102. After a time, the sampling valve 98 is switched to the first flow network so that the volume of fluid in the second metering tube 102 is swept by the carrier fluid through the detector inlet port 108 to the detector. This process is continued until fluid from all of the vessels 12 is analyzed.

Flow Sensing & Control

Referring once again to FIG. 1, an important aspect of the screening apparatus 10 is that it apportion the test fluid about equally between each of the vessels 12. This is important because the extent of change in the test fluid following contact with a library member depends on, among other things, the time a given amount of test fluid contacts the library member.

The test fluid is split about equally among the vessels 12 in at least two ways. First, flow restrictors 18 are inserted between the entrance control volume 14 and the vessel 12. Because fluid flow resistance is greatest in the flow restrictors 18 and varies little among individual restrictors 18, the test fluid is apportioned about equally between each of the vessels 12. Furthermore, because the flow restrictors 18 are placed upstream of the vessels 12 in the embodiment shown in FIG. 1, flow rate through the vessels 12 is mainly a function of the applied pressure in the entrance control volume 14, and the pressure in each of the vessels 12 is about equal to the pressure in the exit control volume 16. Thus, the pressure in the vessels 12 can be controlled by adjusting the pressure in the exit control volume 16, generally independently of flow rate through the vessels 12.

Note, however, that one may also place the flow restrictors 18 downstream of the vessels 12. In that case, pressure in each of the vessels 12 is controlled by, and is about equal to, the applied pressure in the entrance control volume 14. Although placing the flow restrictors 18 downstream of the vessels 12 results in tighter coupling of the pressure in the vessels 12 with flow rate, such placement, as discussed below, offers certain advantages, including a simpler fluid handling and detection system.

Second, fluid can be apportioned about equally between the vessels 12 by either replacing or supplementing each of the flow restrictors 18 with individual flow regulators. When used in conjunction with flow restrictors 18, the flow regulators can be located immediately upstream or downstream of the flow restrictors 18.

Figure 7:
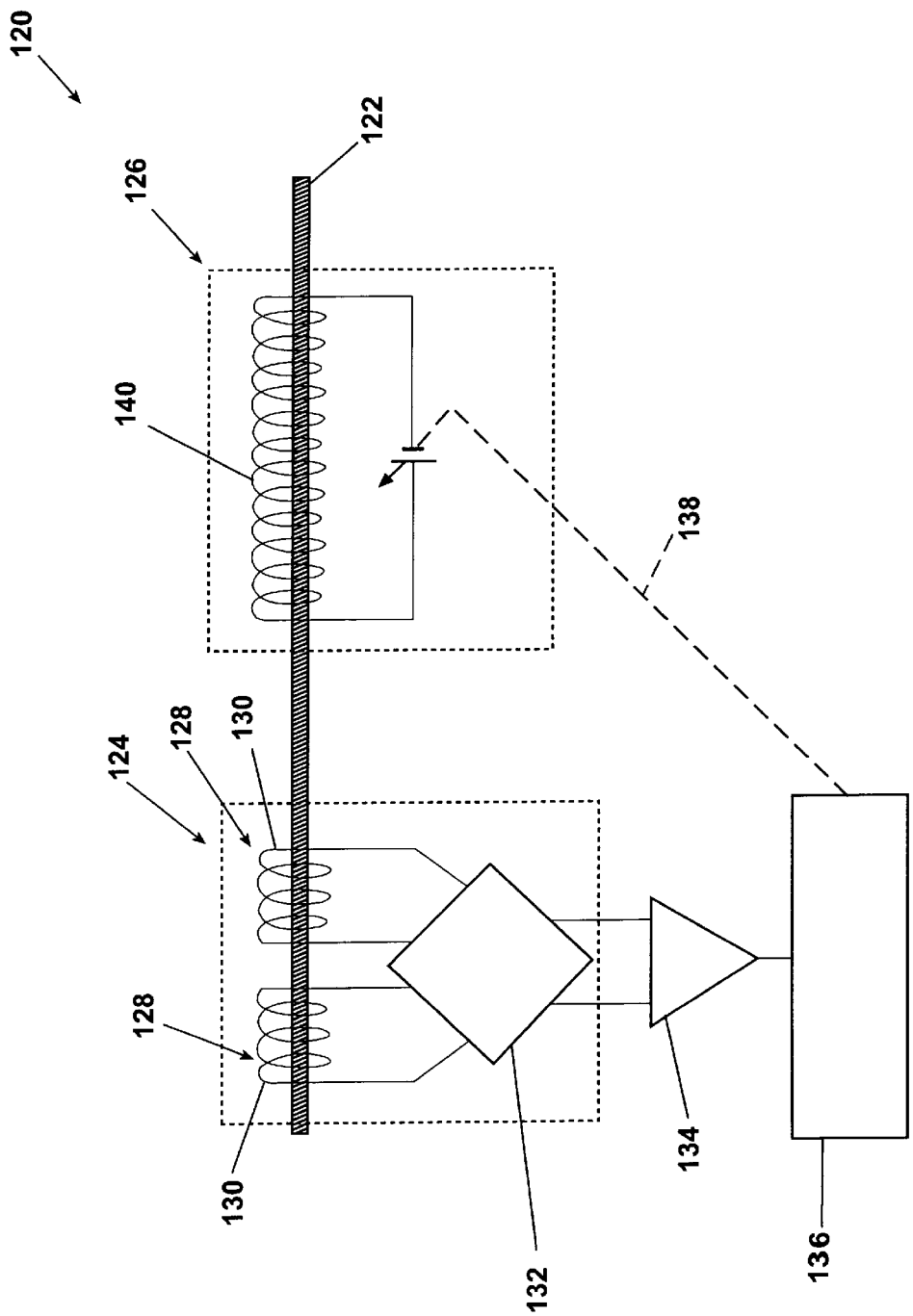
FIG. 7 shows schematically a flow sensor and control device for apportioning fluid equally between vessels of the screening apparatus.

A flow regulator 120 for a single fluid flow 122 is shown schematically in FIG. 7. The device 120 is comprised of a flow sensor 124, which communicates with a flow controller 126. The flow sensor 124 determines mass flow rate of the fluid stream 122 by detecting a temperature difference between two sensor elements 128 located upstream of the flow controller 126.

The two sensor elements 128 are adjacent wire coils 130 surrounding the fluid stream 122, and comprise two arms of a Wheatstone bridge 132. The sensor elements 128 act as heaters and temperature sensors. A constant electrical current is passed through the two wire coils 130, and is converted to heat due to the electrical resistance of the wire. Because the electrical resistance of the wire coils 130 varies with temperature, the coils also function as resistance temperature detectors, or RTDs, which measure the temperature of the fluid stream 122.

In a static fluid, heat from the wire coils 130 results in a uniform axial temperature gradient about a midpoint between the two wire coils 130. However, fluid flow transports heat generated at the wire coils 130 downstream, distorting the temperature gradient so that a temperature difference develops between the two sensor elements 128. The temperature difference results in a change of resistance of the two sensor elements 128, and produces an imbalance across the bridge 132. An amplifier 134 conditions and amplifies this signal, typically 0–5 V dc. An A/D converter and microprocessor 136 converts the 0–5 V dc signal to flow rate data. Based on this data, the microprocessor 136 transmits a digital signal 138 to the flow controller 126.

The flow controller 126 adjusts flow rate in response to the digital signal 138 by changing the heat flux to the fluid stream 122 in a heating zone 140. Because viscosity of a gas, and hence flow resistance, increases with temperature, mass flow through the heating zone 140 of the fluid stream 122 can be increased (decreased) by increasing (decreasing) the temperature of the fluid stream 122. For example, air at 0° C. has a viscosity of 170.8 $\mu$-poises, while air at 74° C. has a viscosity of 210.2 $\mu$-poises. For a narrow cylindrical tube, volumetric flow rate is inversely proportional to gas viscosity. Therefore, for air, a 74° C. change will cause, for a given pressure gradient, about a 10 percent decrease in flow rate. Thus, the rate controller 126 can control up to about 15 percent of the flow range, although it is unable to stop the flow completely.

Parallel Vessel/Reactor Block

Figure 8:
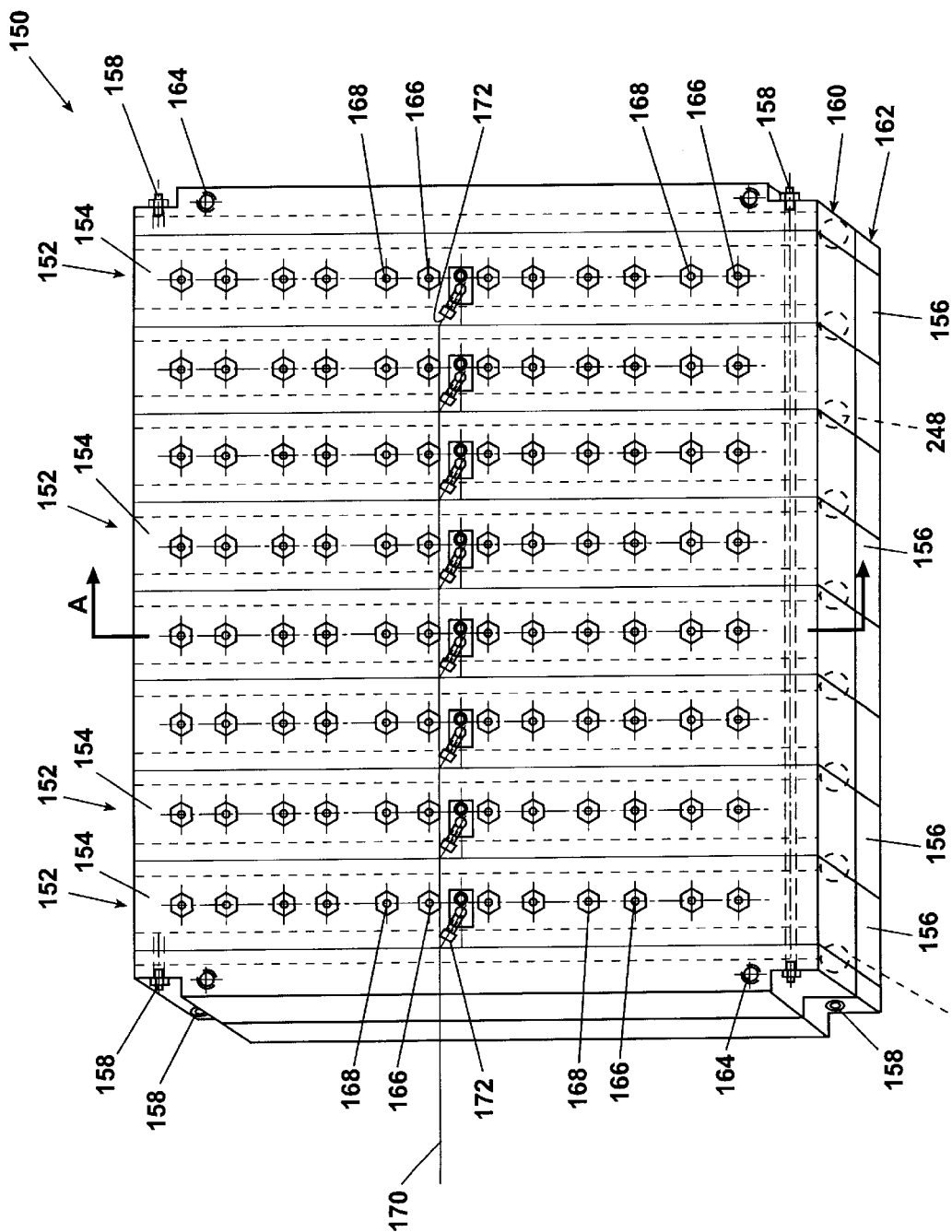
FIG. 8 shows a perspective bottom view of a first embodiment of a vessel assembly.

FIG. 8 shows a bottom view of a first embodiment of a vessel assembly 150 that contains the vessels. The vessels are held within in a rectangular array of wells, which are shown in FIG. 9 and described below. Although the embodiment shown in FIG. 8 is comprised of eight rows 152, each containing six wells and six vessels, the number of rows 152 and the number of wells within each of the rows 152 can be varied. With the embodiment shown in FIG. 8, any multiple of six library members—up to and including forty eight members—can be screened at a time. In general, at least six library members, or at least forty-eight library members are screened.

Each of the rows 152 comprises a separate base segment 154 and cover segment 156 which aids in assembly and replacement of damaged or plugged wells. When base segments 154 and cover segments 156 are clamped together using tie rods 158, they form a base block 160 and a cover block 162, respectively. This construction allows one to remove the cover block as a single body; the base block 160 and the cover block 162 are clamped together using threaded fasteners inserted in bolt holes 164. Each base segment 154 has a plurality of vessel inlet ports 166 and vessel outlet ports 168, that provide fluid flow paths from the exterior of the vessel assembly 150, through the base segment 154, and into the wells and vessels. Wires 170 connect to thermocouples, sensors, and the like, through instrumentation ports 172 in each base segment 154.

FIG. 9 shows a cross section of the vessel assembly 150 along viewing plane "A" of FIG. 8. The vessel assembly 150 is comprised of the cover segment 156 disposed on the base segment 154. The cover 156 and base 154 segments are encased in insulation 182 to lessen heat loss during screening, and to decrease temperature gradients. The base segment 154 of the embodiment shown in FIG. 9 is comprised of six wells 184, each containing one of the vessels 12.

Details of the wells 184 and vessels 12 can be seen in FIG. 10, which provides a close up view of section "B" of FIG. 9. Each of the vessels 12 can hold 10–100 mg of sample 186, depending on the sample 186 density. The vessels 12 are made of stainless steel or quartz, though any material having comparable mechanical strength, resistance to chemical attack, and thermal stability can be used. The vessels 12 shown in FIGS. 9 and 10 are hollow right circular cylinders, each having a fluid permeable upper end 188 and lower end 190. A quartz paper frit 192 in the lower end 190 of each of the vessels 12 holds the sample 186 in place, but allows fluid to pass through. Threaded fasteners 194 secure the cover segment 156, the base segment 154, and hence vessels 12 in place.

FIG. 10 also shows elements for preventing fluid leaks. The lower end 190 of each of the vessels 12 has a polished chamfered surface, which, along with an upper end 196 of each of the outlet ports 160, defines a cavity for accepting a miniature gold o-ring 198. A compressed spring 200 pushes against a vessel cover 202 and the upper end 188 of each of the vessels 12, compressing the o-ring 198. The vessel cover 202 and the base segment 154 have knife edges 204 that contact a copper gasket 206 seated in a groove 208 on the base segment 154. BELLEVILLE washer springs 210, which are med of INCONEL to prevent creeping under high temperature and loading, push against an end wall 212 of a cavity 214 in the cover segment 156, resulting in the knife edge 204 cutting into the gasket 206. The washer springs 210 deliver a sealing force of about 500 pounds per gasket 206. To eliminate handling of loose parts, stops 216 limit the travel of the vessel cover 202 and the washer springs 210, which are retained in the cover segment cavity 214.

FIG. 9 and FIG. 10 show the interaction of the fluid handling system with the vessel 150. Fluid enters the vessel assembly 150 via the flow restriction 14, which are threaded through the vessel into ports 166. Compression fittings 218 provide a fluid-tight seal where each of the flow restrictors 14 penetrate the inlet ports 166. An angled bore 220 channels fluid from the flow restrictors 18 to the upper end 188 of each of the vessels 12. From there, fluid flows downward through the sample 186, passes through the frit 192, and into the outlet conduits 20. Compression fittings 218 prevent fluid from leaking at the interface between each of the outlet conduits 20 and outlet ports 168.

Figure 11:
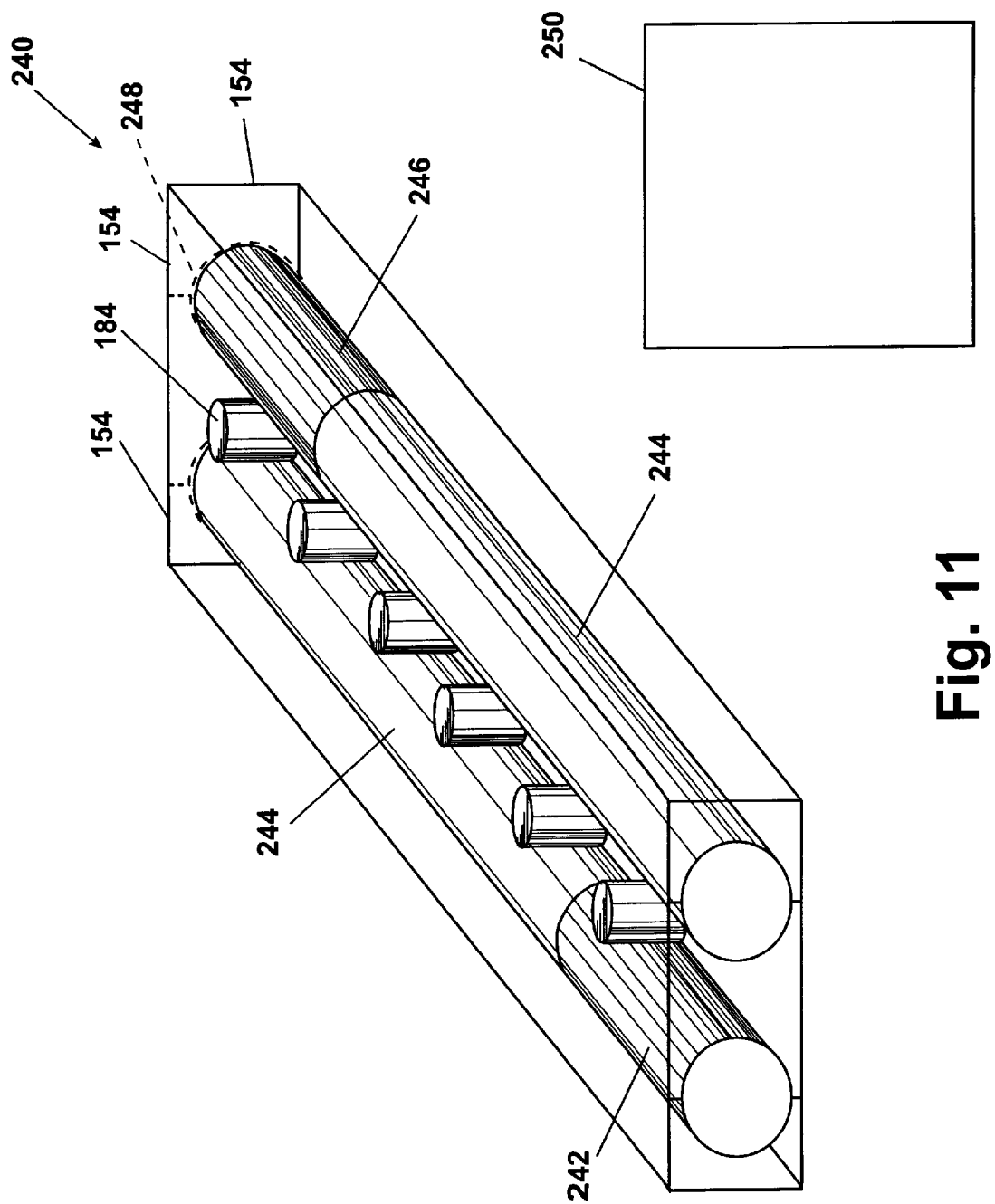
FIG. 11 shows a temperature control system.

Because it is generally necessary to control the temperature at which fluid contacts the samples during screening, the vessel assembly is equipped with a temperature control system 240 shown in FIG. 11. The control system is comprised of elongated 242, second 244 and third 246 heating elements that are sandwiched in gaps 248 (see also FIG. 8) between neighboring base segment 154 (shown in phantom in FIG. 11). The heating elements 242, 244, 246 communicate with PID controllers 250, which adjust heat output in response to data obtained from temperature sensors (not shown) located in cavities adjacent to each of the wells 184. Independent control of the heaters 242, 244, 246 reduces the maximum temperature difference between any two wells 184 to as little as 4° C. at 350° C., and allows for substantially linear temperatures gradients along a row of wells 184.

Figure 12:
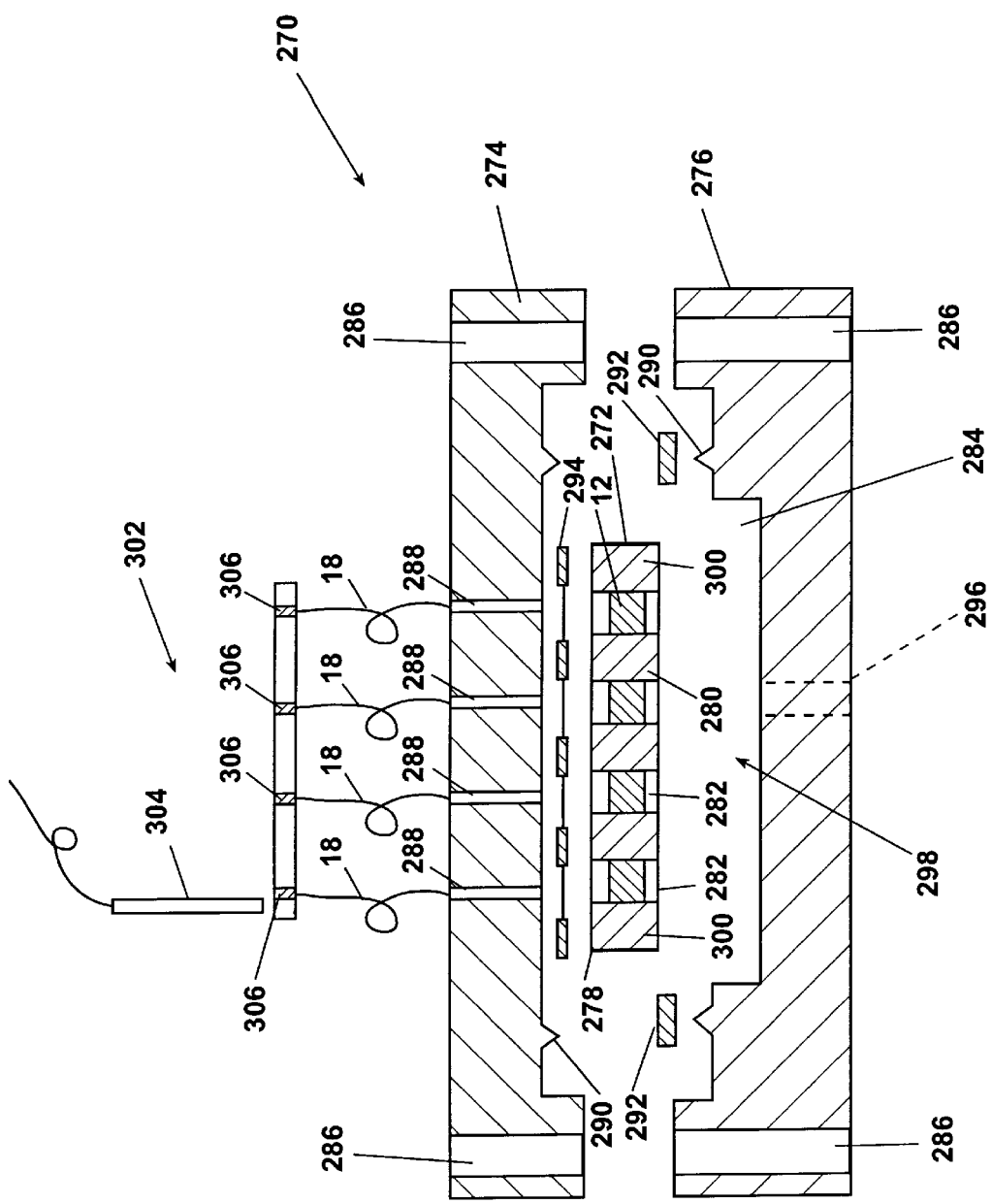
FIG. 12 shows an exploded, cross-sectional view of another embodiment of a vessel assembly and simplified fluid handling system.

FIG. 12 shows an exploded cross section of a second embodiment of a vessel assembly 270 having a simpler fluid handling system. The vessel assembly 270 is comprised of a vessel holder 272 sandwiched between a cover block 274 and a base block 276. The vessel holder 272 has planar upper 278 and lower 280 surfaces, and a plurality of wells 282 perpendicular to the planar surfaces 278, 280. Vessels 12 containing samples are placed within the wells 282.

When assembled, the vessel holder 272 fits within a cavity 284 in the base block 276. Bolts (not shown) are threaded through holes 286 located along the edges of the cover block 274 and base block 276, and provide a compressive force that secures the vessel holder 272 within the vessel assembly 270. An array of holes 288 in the cover block 274, which are in substantial axial alignment with the wells 282, provide a flow path between flow restrictors 18 and the vessels 12.

Because of its simple design, the vessel assembly 270 has modest sealing requirements. The cover block 274 and the base block 276 have knife edges 290 that cut into a copper gasket 292 to prevent fluid from bypassing the wells 282 and the vessels 12. In addition, a quartz paper gasket 294 is disposed on the upper surface 278 of the vessel holder 272 to prevent inter-well diffusion. The tie rods provide sufficient compressive force to secure the vessel holder 272 and to seal the gaskets 292, 294.

During screening, fluid enters the vessel assembly 270 via a fluid port 296. The interior space of the vessel assembly 270, excluding the wells 282, defines a constant-pressure, entrance control volume 298. Projections 300 on the lower surface 280 of the vessel holder 272 create a gap between the base block 276 and the vessel holder 272 and ensure that little or no pressure gradient exists between the fluid port 296 and each of the wells 282. From the entrance control volume 298, the fluid flows upward through the wells 282 and the vessels 12 where it contacts the samples. Holes 288 in the cover block 274 channel the fluid out of the vessel assembly 270 and into the flow restrictors 18, which vent the fluid into an exit control volume 302. The exit control volume 302 is generally any pressure-controlled region external to the vessel assembly 270.

Because the flow restrictors 18 are located downstream of the vessels 12, a screening apparatus using the vessel assembly 270 shown in FIG. 12 has a simple fluid handling system. For example, the fluid distribution valve 76 shown in FIG. 2 cannot be used with the vessel assembly 270 shown in FIG. 12 because the vessels 12 receive fluid directly from the entrance control volume 298; without the distribution valve 76, there is also no need for the inert fluid source 70 in FIG. 2. Furthermore, since test fluid continuously flows through each of the vessels 12 during a screening cycle, the vessel assembly 270 is less useful for screening library members whose performance changes rapidly following initial contact with the test fluid. However, the vessel assembly 270 can screen even rapidly changing library members if each vessel has a separate detector, or if changes in member performance occur over a time scale much longer than the time needed to analyze effluent from individual vessels 12.

Referring again to FIG. 12, test fluid from flow restrictors 18 generally vent directly into the exit control volume 302. A hollow probe 304, having an interior pressure lower than the exit control volume 302, can be placed above the ends 306 of the flow restrictors 18 to sample and convey vessel effluent to a detector (not shown). Alternatively, the flow restrictors 18 can exhaust into inlet ports 92 of the selection valve 94 shown in FIG. 2, to selectively route fluid from one of the vessels 12 to the detector, while dumping fluid from the remaining vessels 12 directly into the exit control volume 302. In either case, the screening apparatus can use the sampling valve 98 of FIG. 2 to send a fixed volume of fluid to the detector without upsetting the volumetric flow rate elsewhere in the fluid handling system.

Flow Matching

Referring again to FIG. 1, members of a combinatorial library are screened by simultaneously contacting a subset of library members with nearly equal amount of test fluid. Test fluid flows in the direction of decreasing pressure: from the entrance control volume 14, through the flow restrictors 18 and vessels 12, and into the exit control volume 16 via outlet conduits 20. A sample bypass 24 diverts test fluid from selected vessels to detectors 26. Because fluid flow resistance is greatest in the flow restrictors 18 and varies little among individual restrictors 18, the test fluid is apportioned about equally between each of the vessels 12. As discussed above, this is important because the extent of change in the test fluid following contact with a library member depends on, among other things, the time a given amount of test fluid contacts the library member.

Besides ensuring that the greatest resistance to fluid flow occurs in the flow restrictors 18, one can improve the accuracy of screening by matching flow rates in each flow path between the entrance control volume 14 and the exit control volume 16. This can be achieved by equating each flow path's conductance. Conductance, which has the units ml.min$^{-1}$, is the ratio of fluid flux, in pressure-volume units, to the pressure difference between the ends of a flow segment. Conductance is a function of the segment geometry, and a function of the pressure, temperature, and properties of the gas. When two or more segments are connected in parallel, the overall conductance C is given by the equation $$C = \sum_i C_i; \qquad \text{I}$$

when two or more segments are connected in series, the overall conductance is given by the equation $$\frac{1}{C} = \sum_i \frac{1}{C_i}. \qquad \text{II}$$

EXAMPLES

The following examples are intended as illustrative and non-limiting, and represent specific embodiments of the present invention.

Example 1

Flow Matching

Figure 13:
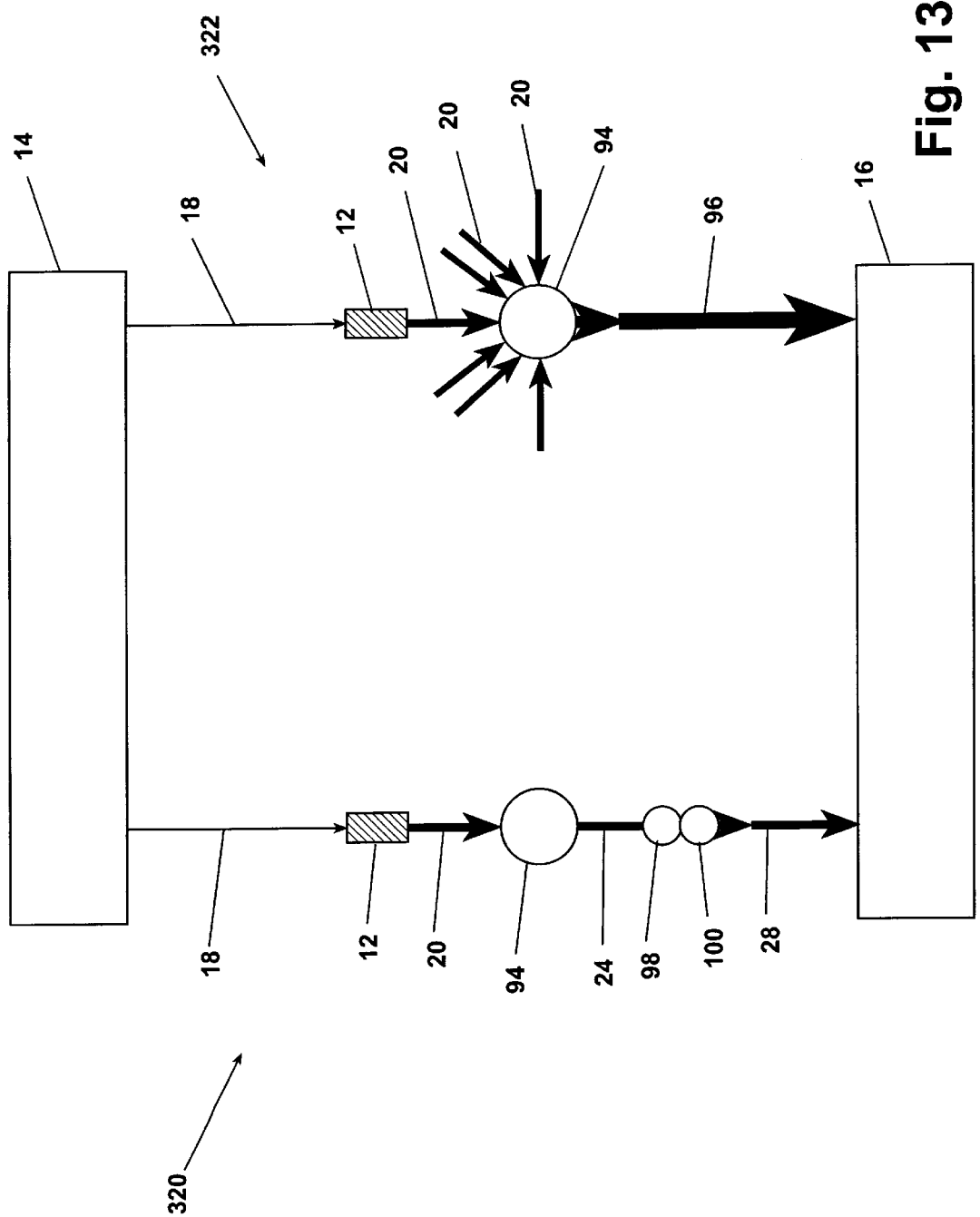
FIG. 13 schematically shows flow paths for the fluid handling system illustrated in FIG. 2.

FIG. 13 schematically shows flow paths for the fluid handling system illustrated in FIG. 2. The selection valve 94 in FIG. 13 diverts fluid into two groups of fluid streams: a first flow path 320, which includes the sample bypass 24, sampling valve 98, first metering tube 100, and return line 28, and a second flow path 322, which vents fluid directly into the exit control volume 16 via the common exhaust port 96.

Table 1 lists conductance for each segment of the two flow paths based on air at standard temperature and pressure. Conductance for the selection valve 94 and the sampling valve 98, an 8-port injection valve, were calculated from data obtained from the manufacturer, VALCO, for valves having $\frac{1}{16}$ inch fittings and 0.030 inch diameter bore size. According to VALCO, applying air at 5 psig results across either valve results in a flux of 1000 atm.ml.min$^{-1}$, which corresponds to a one-pass conductance of 1000·14.7/5 ml.min$^{-1}$ or 3000 ml.min$^{-1}$. The conductance of the first metering tube 100, sample bypass 24, and exhaust port 96 were calculated from a well know equation for viscous flow of air at 298K in long cylindrical tubes.

$$C = \frac{10.8 \times 10^6 D^4}{L} \overline{P}, \text{ ml} \cdot \text{min}^{-1}. \quad \text{III}$$

In equation III, D is the inner diameter of the tube, L is its length, and $\overline{P}$ is the average pressure, in Torr, which is here taken to be 760 Torr.

TABLE 1

Conductance, C, of air at 298K for each flow segment comprising the first flow path 320 and the second flow path 322.

| Segment | C ml · min$^{-1}$ | D inches | L cm |
|---|---|---|---|
| selection valve 94 | 3000 | — | — |
| sampling valve 98 | 3000 | — | — |
| first metering tube 100 | 2200 | 0.020 | 24.6 |
| sample bypass 24 | 5600 | 0.030 | 50 |
| exhaust port 96 | 88 × 10$^3$ | 0.040 | 10 |
| return line 28 | 1300[1] | 0.015 | 13 |

[1]Calculated from equation IV to match flow within each of the flow paths 320, 322.

In order to match conductance in each flow path, equations I and II require that for one first flow path 320 and each of the seven second flow paths 322 shown in FIG. 13, $$\frac{3}{3000} + \frac{1}{2200} + \frac{1}{5600} + \frac{1}{C_R} = \frac{1}{3000/7} + \frac{1}{88 \times 10^3/7} \quad \text{IV}$$

where the first term on the left-hand side of equation IV corresponds to the flow impedance due to one pass through the selection valve 94 and two passes through the sampling valve 98, and where $C_R$ is the conductance of the return line 28. Solving equation IV for $C_R$ yields a flow conductance of about 1300 ml.min$^{-1}$, which, on substitution into equation III implies that a tube having D=0.015 inches and L=13 cm can be used to match flow in each of the flow paths 320, 322.

Note that the conductance of the flow restrictors 18 and vessels 12 are much less that the conductance of the flow segments listed in Table 1. For example, a stainless steel frit available from VALCO under the trade name 2FR2, and having a 0.125 inch outer diameter, a 1 mm thickness, and a 2 micron pore size, will pass 60 ml.min$^{-1}$ of air at 298K due to a 1 atmosphere pressure difference across the frit. Loading each of the vessels 12 with library members may halve the conductance of the vessels 12 to about 30 ml.min$^{-1}$, which is still much less that the conductance of the segments listed in Table 1. Similarly, using flow restrictors 18 comprised of capillary tubing having D=0.005 inches and L=100 cm results in a conductance of 4.3 ml.min$^{-1}$, which is much smaller than either the conductance of the vessels 12 or the flow segments listed in Table 1.

Example 2

Screening Methodology Using 48-Vessel Screening Apparatus

Figure 14:
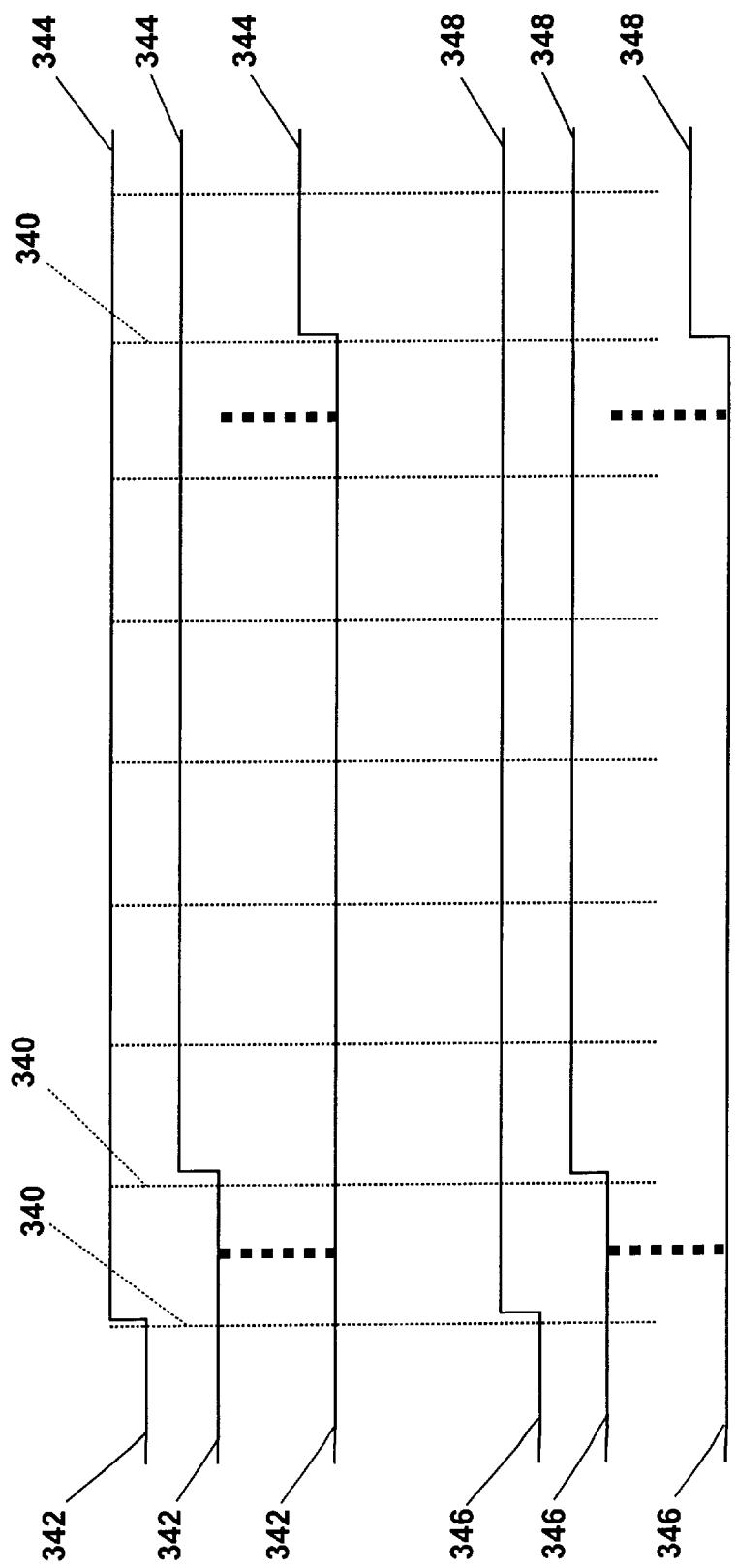
FIG. 14 shows gas distribution and temperature control as a function of time for a 48-vessel screening apparatus.

FIG. 14 shows gas distribution and temperature control as a function of time for the 48-vessel screening apparatus 10 shown in FIG. 1. The 48-vessel screening apparatus uses a fluid handling system, vessel assembly, and temperature control system like those shown in FIG. 2, FIGS. 8–10, and FIG. 11, respectively. The vessels are arranged in eight rows, each of the rows having six vessels. Thus, the eight vessels 12 shown in FIG. 2 correspond to the first of six vessels of each row. Furthermore, flow restrictors 18 connect each of the first outlet ports 88 to the other five vessels (not shown) in each row. In this way, fluid flows from a single outlet port 88 to all six vessels of a particular row simultaneously.

Row-by-row contacting is shown schematically in FIG. 14. Vertical lines 340 indicate the time at which the distribution valve 76 of FIG. 2 starts to provide test fluid to a particular row of vessels. First horizontal lines 342 indicate the flow of an inert fluid through a row of vessels, while second horizontal lines indicate the flow of a test fluid through a row or vessels. Similarly, third horizontal lines 346 and fourth horizontal lines 348 indicate, respectively, no heating and heating of row vessels.

Figure 15:
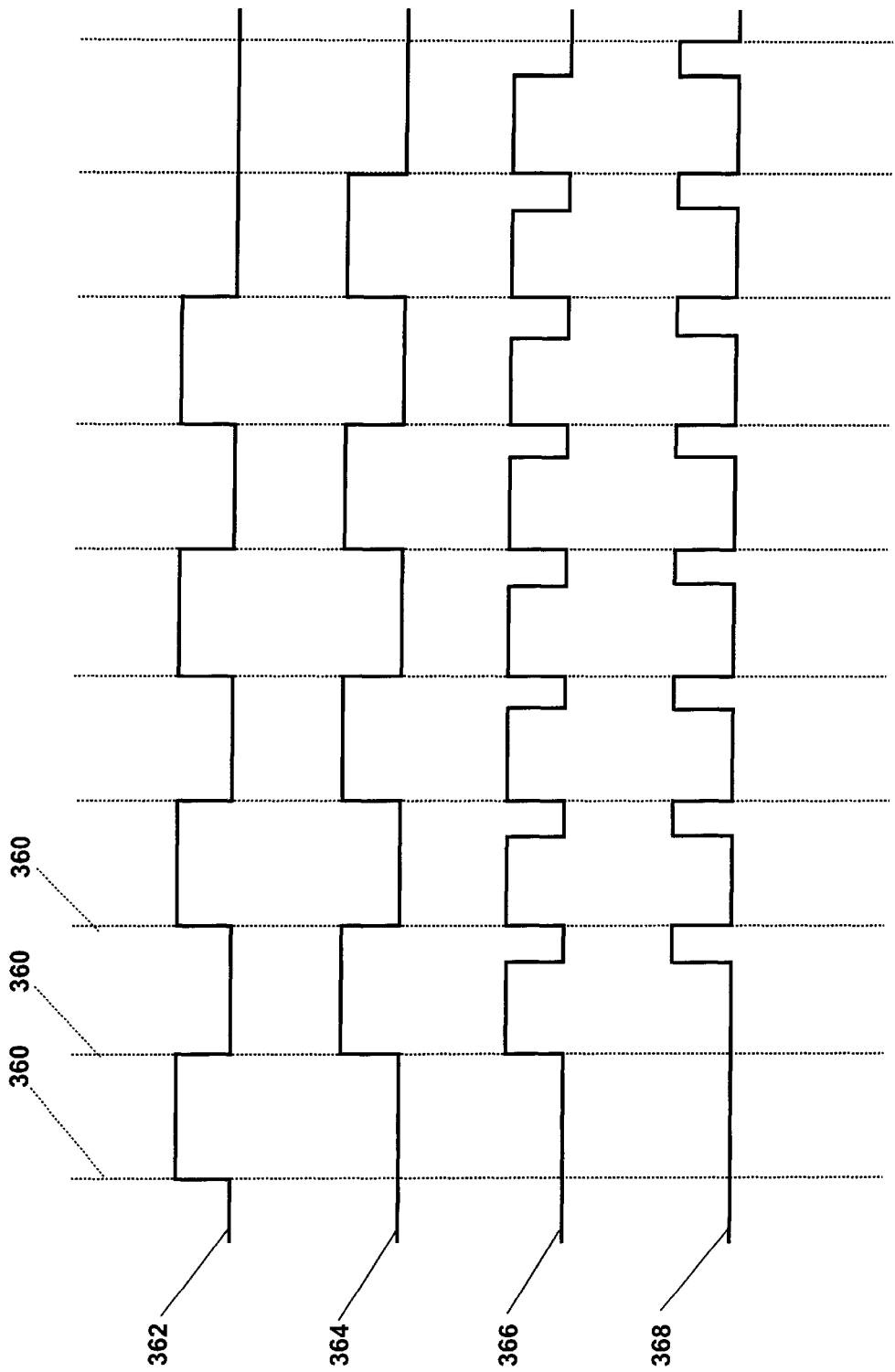
FIG. 15 illustrates sampling and detection times for a 48-vessel screening apparatus using two, 3-channel gas chromatographs.

FIG. 15 illustrates sampling and detection times for the 48-vessel screening apparatus using two, 3-channel GCs. Since library members undergo row-by-row contacting, the screening apparatus uses six selection valves 94, six sampling valves 98, and six first 100 and second 102 metering tubes of types shown in FIG. 2. Vertical lines 360 indicate the time at which the sampling valve fills the first or the second metering tube with test fluid, and the time at which the sampling valve injects test fluid from the first or the second metering tube into a GC separation column. First 362 and second 364 horizontal lines show GC separation and data reduction, respectively. In FIG. 15, the time interval between each vertical line 360 corresponds to four minutes. Therefore, it takes about 36 minutes to complete the screening and detection of 48 library members. Thus, the average time for evaluating a library member is about 36/48 or 0.75 minutes.

Example 3

Catalyst Screening

A six-vessel screening apparatus was used to screen library members based on their ability to catalyze the conversion of ethane to ethylene. The apparatus employed fluid handling and temperature control systems similar to those shown in FIG. 2, and FIG. 11, respectively. Furthermore, the screening apparatus comprised one base segment 154 of the vessel assembly 150 shown in FIG. 8.

High purity ethane and 14.4% $O_2$ in $N_2$ were obtained from MATHESON. Pure $N_2$ was obtained from an in-house supply line. After loading catalysts, the fluid handling system was purged for ten minutes with $N_2$ to remove $O_2$. Next, the fluid handling system was filled with ethane for another ten minutes. GC detection was carried out to ensure that the ethane level had reached 95%. The $O_2/N_2$ mixture was then added so that the reactant flow rate was 1.04 sccm per reactor vessel, and the gas composition was 40% ethane, 8.6% $O_2$, and 51.4% $N_2$. The stability of gas flow was measured periodically by GC.

The screening apparatus used two VARIAN 3800, 3-channel GCs to detect ethylene in vessel effluent. Each of the three channels contained 6-inch HAYESEP columns, methanizers, and flame-ionization detectors. Carbon monoxide, $CO_2$, ethylene, and ethane were separated to baseline in three minutes.

The responses of the flame ionization detector and the methanizer were calibrated using a standard gas mixture containing 2.0% CO, 2.0% $CO_2$, 6.0% ethylene, 30.0% ethane, 4.0% $O_2$, and the balance, $N_2$. Five calibration experiments were carried out to generate calibration coefficients.

Reactor (vessel) temperature was controlled to 300° C., and reactions were carried out at 15 psia.

Table 2 lists conversion and selectivity for the dehydrogenation of ethane. One hundred mg of the same catalyst were loaded into each of the 6 reaction vessels. The conversion and selectivity data agree with available data for the same catalyst and the same reaction conditions. Moreover, the present data was obtained using 140 times less catalyst.

TABLE 2

Results of catalyst screening using a first catalyst.

| Reactor | 1 | 2 | 3 | 4 | 5 | 6 |
|---|---|---|---|---|---|---|
| Temperature, ° C. | 278.5 | 300.9 | 300.0 | 298.7 | 294.4 | 283.9 |
| Conversion, % | 5.87 | 6.75 | 6.75 | 6.25 | 6.23 | 5.07 |
| Selectivity to Ethylene | 83.75 | 83.23 | 83.41 | 81.81 | 82.63 | 84.53 |

In a second embodiment, catalysts in vessels 4–6 from the previous experiment were used again. They were cooled to ambient temperature, and exposed briefly to air. The other three vessels, 1–3, were loaded with a second, fresh catalyst. Table 3 lists data for the second set of reactions, which show that the use of the second catalyst results in an order of magnitude lower conversion.

TABLE 3

Results of catalyst screening using a first and second catalyst.

| Reactor | 1 | 2 | 3 | 4 | 5 | 6 |
|---|---|---|---|---|---|---|
| Temperature, ° C. | 285.5 | 300.9 | 301.2 | 300.0 | 295.8 | 287.2 |
| Conversion, % | 0.45 | 0.51 | 0.50 | 5.85 | 5.92 | 4.94 |
| Selectivity to Ethylene | 60.96 | 61.04 | 62.54 | 81.37 | 82.29 | 83.71 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. An apparatus for screening members of a library, the apparatus comprising at least six vessels for receiving library members, each of the at least six vessels having an inlet and an outlet, a detector for analyzing vessel effluent, a fluid handling system for providing fluid flow simultaneously through the at least six vessels, and a sampling probe selectively positioned to sample vessel effluent and adapted to transport sampled fluid to the detector, the fluid handling system comprising an entrance control volume in fluid communication with the inlet of each of the at least six vessels, an exit control volume in fluid communication with the outlet of each of the at least six vessels, and at least six flow restrictors, each of the at least six flow restrictors providing fluid communication between one of the at least six vessels and (i) the entrance control volume or alternatively, (ii) the exit control volume, the resistance to fluid flow in the fluid handling system being greatest in the flow restrictors and the resistance to flow in each of the at least six flow restrictors being approximately the same, such that maintaining a higher pressure in the entrance control volume than in the exit control volume results in simultaneous fluid flow through the at least six vessels that is apportioned approximately equally between each of the at least six vessels.

2. An apparatus for screening members of a library, the apparatus comprising at least six vessels for receiving library members, each of the at least six vessels having an inlet and an outlet, a detector for analyzing vessel effluent, and a fluid handling system for providing fluid flow simultaneously through the at least six vessels, the fluid handling system comprising an entrance control volume in fluid communication with the inlet of each of the at least six vessels, an exit control volume in fluid communication with the outlet of each of the at least six vessels, at least six flow restrictors, each of the at least six flow restrictors providing fluid communication between one of the at least six vessels and (i) the entrance control volume or alternatively, (ii) the exit control volume, the resistance to fluid flow in the fluid handling system being greatest in the flow restrictors and the resistance to flow in each of the at least six flow restrictors being approximately the same, such that maintaining a higher pressure in the entrance control volume than in the exit control volume results in simultaneous fluid flow through the at least six vessels that is apportioned approximately equally between each of the at least six vessels, at least six outlet conduits and a selection valve, the outlet conduits providing fluid communication between the outlet of each of the at least six vessels and the selection valve, a sample bypass and a sampling valve, the sample bypass providing fluid communication between the selection valve and the sampling valve, and a return line providing fluid communication between the sampling valve, and the exit control volume, the selection valve being adapted to divert fluid from a selected vessel to the sample bypass while allowing fluid from non-selected vessels to flow to the exit control volume, the sampling valve being adapted to provide selective fluid communication between the sample bypass and the return line, and between the sample bypass and the detector.

3. An apparatus for screening members of a library, the apparatus comprising
at least six vessels for receiving library members, each of the at least six vessels having an inlet and an outlet,
a detector for analyzing vessel effluent, and
a fluid handling system for providing fluid flow simultaneously through the at least six vessels, the fluid handling system comprising
an entrance control volume in fluid communication with the inlet of each of the at least six vessels,
an exit control volume in fluid communication with the outlet of each of the at least six vessels,
at least six flow restrictors, each of the at least six flow restrictors providing fluid communication between one of the at least six vessels and (i) the entrance control volume, or alternatively, (ii) the exit control volume, the resistance to fluid flow in the fluid handling system being greatest in the flow restrictors and the resistance to flow in each of the at least six flow restrictors being approximately the same, such that maintaining a higher pressure in the entrance control volume than in the exit control volume results in simultaneous fluid flow through the at least six vessels that is apportioned approximately equally between each of the at least six vessels, and
a fluid distribution valve having a first valve portion, a second valve portion, and a plurality of exhaust conduits providing fluid communication between the fluid distribution valve and the exit control volume, the first valve portion providing selective fluid communication between a test fluid source and the flow restrictors or the vessel inlets and between the test fluid source and the exhaust conduits, the second valve portion providing selective fluid communication between an inert fluid source and the flow restrictors or the vessel inlets and between the inert fluid source and the exhaust conduits, the resistance to fluid flow in each of the exhaust conduits being approximately the same and being about equal to the resistance to flow in each of the flow restrictors, so that fluid flow is apportioned approximately equally between each of the vessels and exhaust conduits.

4. An apparatus for screening members of a library, the apparatus comprising
an assembly containing at least six vessels for receiving library members, each of the at least six vessels having an inlet and an outlet, the assembly comprising
a base block having a planar top surface and a bottom surface, the top surface of the base block having a plurality of wells formed therein,
a cover block having a planar bottom surface, the bottom surface of the cover block being disposed on the top surface of the base block and having a plurality of depressions formed therein, the cover block being removably attached to the base block with each of the plurality of depressions being in substantial alignment with one of the wells, such that the aligned depressions and wells form cavities for containing the vessels, and
vessel inlet ports and vessel outlet ports located on the bottom surface of the base block, each of the vessel inlet ports providing fluid communication with the inlet of only one of the vessels, and each of the vessel outlet ports providing fluid communication with the outlet of only one of the vessels,
a detector for analyzing vessel effluent, and
a fluid handling system for providing fluid flow simultaneously through the at least six vessels, the fluid handling system comprising
an entrance control volume in fluid communication with the inlet of each of the at least six vessels,
an exit control volume in fluid communication with the outlet of each of the at least six vessels,
at least six flow restrictors, each of the at least six flow restrictors providing fluid communication between one of the at least six vessels and (i) the entrance control volume, or alternatively, (ii) the exit control volume, the resistance to fluid flow in the fluid handling system being greatest in the flow restrictors and the resistance to flow in each of the at least six flow restrictors being approximately the same, such that maintaining a higher pressure in the entrance control volume than in the exit control volume results in simultaneous fluid flow through the at least six vessels that is apportioned approximately equally between each of the at least six vessels.

5. An apparatus for screening members of a library, the apparatus comprising:
a plurality of vessels for receiving library members, each of the plurality of vessels having an inlet and an outlet;
a detector for analyzing vessel effluent; and
a fluid handling system comprising:
an entrance control volume and a plurality of flow restrictors, the flow restrictors providing fluid communication between the entrance control volume and the inlet of each of the plurality of vessels,
a plurality of outlet conduits and a selection valve, the outlet conduits providing fluid communication between the outlet of each of the plurality of vessels and the selection valve;
a sample bypass and a sampling valve, the sample bypass providing fluid communication between the selection valve and the sampling valve; and
a return line and an exit control volume, the return line providing fluid communication between the sampling valve and the exit control volume,
the selection valve being adapted to divert fluid from a selected vessel to the sample bypass while allowing fluid from non-selected vessels to flow to the exit control volume,
the sampling valve providing selective fluid communication between the sample bypass and the detector, and between the sample bypass and the return line;
the resistance to fluid flow in the fluid handling system being greatest in the flow restrictors and the resistance to flow in each of the plurality of flow restrictors being approximately the same, so that maintaining a higher pressure in the entrance control volume than in the exit control volume results in simultaneous fluid flow from the entrance control volume to the exit control volume that is apportioned approximately equally between each of the plurality of vessels.

6. A reactor for evaluating catalytic performance of members of a library, the reactor comprising
a plurality of reaction vessels for receiving library members, each of the plurality of reaction vessels having an inlet and an outlet,
a fluid handling system for providing fluid flow simultaneously through the plurality of reaction vessels, and
a sampling probe selectively positioned to sample vessel effluent and adapted to transport sampled fluid to a detector, the fluid handling system comprising an entrance control volume in fluid communication with the inlet of each of the plurality of reaction vessels, an exit control volume in fluid communication with the outlet of each of the plurality of reaction vessels, and a plurality of flow restrictors, each of the plurality of flow restrictors providing fluid communication between one of the plurality of reaction vessels and (i) the entrance control volume, or alternatively, (ii) the exit control volume, the resistance to fluid flow in the fluid handling system being greatest in the flow restrictors and the resistance to flow in each of the plurality of flow restrictors being approximately the same, so that maintaining a higher pressure in the entrance control volume than in the exit control volume results in simultaneous fluid flow through the plurality of reaction vessels that is apportioned approximately equally between each of the plurality of reaction vessels.

7. A reactor for evaluating catalytic performance of members of a library, the reactor comprising a plurality of reaction vessels for receiving library members, each of the plurality of reaction vessels having an inlet and an outlet, and a fluid handling system for providing fluid flow simultaneously through the plurality of reaction vessels, the fluid handling system comprising an entrance control volume in fluid communication with the inlet of each of the plurality of reaction vessels, an exit control volume in fluid communication with the outlet of each of the plurality of reaction vessels, a plurality of flow restrictors, each of the plurality of flow restrictors providing fluid communication between one of the plurality of reaction vessels and (i) the entrance control volume, or alternatively, (ii) the exit control volume, the resistance to fluid flow in the fluid handling system being greatest in the flow restrictors and the resistance to flow in each of the plurality of flow restrictors being approximately the same, so that maintaining a higher pressure in the entrance control volume than in the exit control volume results in simultaneous fluid flow through the plurality of reaction vessels that is apportioned approximately equally between each of the plurality of reaction vessels, a plurality of outlet conduits and a selection valve, the outlet conduits providing fluid communication between the outlet of each of the plurality of reaction vessels and the selection valve, a sample bypass and a sampling valve, the sample bypass providing fluid communication between the selection valve and the sampling valve, and a return line providing fluid communication between the sampling valve and the exit control volume, the selection valve being adapted to divert fluid from a selected reaction vessel to the sample bypass while allowing fluid from non-selected vessels to flow to the exit control volume, the sampling valve being adapted to provide selective fluid communication between the sample bypass and the return line, and between the sample bypass and a detector.

8. A reactor for evaluating catalytic performance of members of a library, the reactor comprising a plurality of reaction vessels for receiving library members, each of the plurality of reaction vessels having an inlet and an outlet, a fluid handling system for providing fluid flow simultaneously through the plurality of reaction vessels, the fluid handling system comprising an entrance control volume in fluid communication with the inlet of each of the plurality of reaction vessels, an exit control volume in fluid communication with the outlet of each of the plurality of reaction vessels, and a plurality of flow restrictors, each of the plurality of flow restrictors providing fluid communication between one of the plurality of reaction vessels and (i) the entrance control volume, or alternatively, (ii) the exit control volume, the resistance to fluid flow in the fluid handling system being greatest in the flow restrictors and the resistance to flow in each of the plurality of flow restrictors being approximately the same, so that maintaining a higher pressure in the entrance control volume than in the exit control volume results in simultaneous fluid flow through the plurality of reaction vessels that is apportioned approximately equally between each of the plurality of reaction vessels, and a fluid distribution valve having a first valve portion, a second valve portion, and a plurality of exhaust conduits providing fluid communication between the fluid distribution valve and the exit control volume, the first valve portion providing selective fluid communication between a test fluid source and the flow restrictors or the vessel inlets and between the reactive fluid source and the exhaust conduits, the second valve portion providing selective fluid communication between an inert fluid source and the flow restrictors or the vessel inlets and between the inert fluid source and the exhaust conduits, the resistance to fluid flow in each of the exhaust conduits being approximately the same and being about equal to the resistance to flow in each of the flow restrictors, so that fluid flow is apportioned approximately equally between each of the vessels and exhaust conduits.

9. A reactor for evaluating catalytic performance of members of a library, the reactor comprising an assembly containing a plurality of reaction vessels for receiving library members, each of the plurality of reaction vessels having an inlet and an outlet, the assembly comprising a base block having a planar top surface and a bottom surface, the top surface of the base block having a plurality of wells formed therein, a cover block having a planar bottom surface, the bottom surface of the cover block being disposed on the top surface of the base block and having a plurality of depressions formed therein, the cover block being removably attached to the base block with each of the plurality of depressions being in substantial alignment with one of the wells, such that the aligned depressions and wells form cavities for containing the vessels, and vessel inlet ports and vessel outlet ports located on the bottom surface of the base block, each of the vessel inlet ports providing fluid communication with the inlet of only one of the vessels, and each of the vessel outlet ports providing fluid communication with the outlet of only one of the vessels, and a fluid handling system for providing fluid flow simultaneously through the plurality of reaction vessels, the fluid handling system comprising an entrance control volume in fluid communication with the inlet of each of the plurality of reaction vessels, an exit control volume in fluid communication with the outlet of each of the plurality of reaction vessels, and a plurality of flow restrictors, each of the plurality of flow restrictors providing fluid communication between one of the plurality of reaction vessels and (i) the entrance control volume, or alternatively, (ii) the exit control volume, the resistance to fluid flow in the fluid handling system being greatest in the flow restrictors and the resistance to flow in each of the plurality of flow restrictors being approximately the same, so that maintaining a higher pressure in the entrance control volume than in the exit control volume results in simultaneous fluid flow through the plurality of reaction vessels that is apportioned approximately equally between each of the plurality of reaction vessels.

10. An apparatus for screening members of a library, the apparatus comprising:

an assembly containing at least six vessels for receiving library members, each of the at least six vessels having an inlet and an outlet, the assembly comprising a base block having a planar top surface and a bottom surface, the top surface of the base block having a plurality of wells formed therein, a cover block having a planar bottom surface, the bottom surface of the cover block being disposed on the top surface of the base block and having a plurality of depressions formed therein, the cover block being removably attached to the base block with each of the plurality of depressions being in substantial alignment with one of the wells, such that the aligned depressions and wells form cavities for containing the vessels, a vessel inlet port located on the bottom surface of the base block, and vessel outlet ports located on the top surface of the cover block, the vessel inlet port providing fluid communication with an entrance control volume that provides fluid communication with the inlets of the vessels, each of the vessel outlet ports providing fluid communication with the outlet of only one of the vessels, a detector for analyzing vessel effluent, and a fluid handling system for providing fluid flow simultaneously through the at least six vessels, the fluid handling system comprising:

an entrance control volume in fluid communication with the inlet of each of the at least six vessels, an exit control volume in fluid communication with the outlet of each of the at least six vessels, at least six flow restrictors, each of the at least six flow restrictors providing fluid communication between one of the at least six vessels and (i) the entrance control volume, or alternatively, (ii) the exit control volume, the resistance to fluid flow in the fluid handling system being greatest in the flow restrictors and the resistance to flow in each of the at least six flow restrictors being approximately the same, such that maintaining a higher pressure in the entrance control volume than in the exit control volume results in simultaneous fluid flow through the at least six vessels that is apportioned approximately equally between each of the at least six vessels.

11. A reactor for evaluating catalytic performance of members of a library, the reactor comprising an assembly containing a plurality of reaction vessels for receiving library members, each of the plurality of reaction vessels having an inlet and an outlet, the assembly comprising a base block having a planar top surface and a bottom surface, the top surface of the base block having a plurality of wells formed therein, a cover block having a planar bottom surface, the bottom surface of the cover block being disposed on the top surface of the base block and having a plurality of depressions formed therein, the cover block being removably attached to the base block with each of the plurality of depressions being in substantial alignment with one of the wells, such that the aligned depressions and wells form cavities for containing the vessels, and a vessel inlet port located on the bottom surface of the base block, and vessel outlet ports located on the top surface of the cover block, the vessel inlet port providing fluid communication with an entrance control volume that provides fluid communication with the inlets of the vessels, each of the vessel outlet ports providing fluid communication with the outlet of only one of the vessels, and a fluid handling system for providing fluid flow simultaneously through the plurality of reaction vessels, the fluid handling system comprising:

an entrance control volume in fluid communication with the inlet of each of the plurality of reaction vessels, an exit control volume in fluid communication with the outlet of each of the plurality of reaction vessels, and a plurality of flow restrictors, each of the plurality of flow restrictors providing fluid communication between one of the plurality of vessels and (i) the entrance control volume, or alternatively, (ii) the exit control volume, the resistance to fluid flow in the fluid handling system being greatest in the flow restrictors and the resistance to flow in each of the plurality of flow restrictors being approximately the same, so that maintaining a higher pressure in the entrance control volume than in the exit control volume results in simultaneous fluid flow through the plurality of vessels that is apportioned approximately equally between each of the plurality of reaction vessels.

12. An apparatus for screening catalysts, the apparatus comprising:

a plurality of reaction vessels for receiving catalysts, each of the plurality of reaction vessels having an inlet and an outlet, a fluid handling system for providing fluid flow simultaneously through the plurality of reaction vessels, a detector for analyzing vessel effluent, and a sampling probe selectively positioned to sample reaction vessel effluent and adapted to transport the sampled fluid to the detector, the fluid handling system comprising an entrance control volume in fluid communication with the inlet of each of the plurality of reaction vessels, an exit control volume in fluid communication with the outlet of each of the plurality of reaction vessels, and a plurality of flow restrictors or regulators, each of the plurality of flow restrictors or regulators providing fluid communication between one of the plurality of reaction vessels and (i) the entrance control volume, or alternatively, (ii) the exit control volume, the flow restrictors or regulators being adapted such that maintaining a higher pressure in the entrance control volume than in the exit control volume results in simultaneous fluid flow through the reaction vessels that is apportioned approximately equally between each of the plurality of reaction vessels.

13. An apparatus for screening catalysts, the apparatus comprising:
   a plurality of reaction vessels for receiving catalysts, each of the plurality of reaction vessels having an nlet and an outlet;
   a fluid handling system for providing fluid flow simultaneously through the plurality of reaction vessels; and
   a detector for analyzing reaction vessel effluent,
   the fluid handling system comprising
      an entrance control volume in fluid communication with the inlet of each of the plurality of reaction vessels,
      an exit control volume in fluid communication with the outlet of each of the plurality of reaction vessels,
      a plurality of flow restrictors or regulators, each of the plurality of flow restrictors or regulators providing fluid communication between one of the plurality of reaction vessels and (i) the entrance control volume, or alternately, (ii) the exit control volume,
      a plurality of outlet conduits and a selection valve, the outlet conduits providing fluid communication between the outlet of each of the plurality of reaction vessels and the selection valve,
      a sample bypass and a sampling valve, the sample bypass providing fluid communication between the selection valve and the sampling valve, and
      a return line providing fluid communication between the sampling valve and the exit control volume,
      the selection valve being adapted to divert fluid from a selected vessel to the sample bypass while allowing fluid from non-selected vessels to flow to the exit control volume,
      the sampling valve being adapted to provide selective fluid communication between the sample bypass and the return line, and between the sample bypass and the detector,
      the flow restrictors or regulators being adapted such that maintaining a higher pressure in the entrance control volume than in the exit control volume results in simultaneous fluid flow through the reaction vessels that is apportioned approximately equally between each of the plurality of reaction vessels.

14. An apparatus for screening catalysts, the apparatus comprising
   two or more assemblies, each of the two or more assemblies containing a plurality of reaction vessels for receiving catalysts, each of the plurality of reaction vessels having an inlet and an outlet,
   a fluid handling system for providing fluid flow simultaneously through the plurality of reaction vessels within an assembly, and for providing fluid flow sequentially between the reaction vessels of different assemblies,
   a detector for analyzing vessel effluent,
   the fluid handling system comprising
      an entrance control volume in fluid communication with a fluid distribution valve,
      the fluid distribution valve providing selective fluid communication between the entrance control volume and a plurality of distribution valve outlet ports, each of the plurality of distribution valve outlet ports being in fluid communication with the plurality of reaction vessels within one of the two or more assemblies, such that a fluid can be sequentially directed into one of the distribution valve outlet ports, and then simultaneously through the plurality of reaction vessels of the assembly associated with the selected outlet port,
      an exit control volume in fluid communication with the outlet of each of the plurality of reaction vessels, and
      a plurality of flow restrictors or regulators, each of the plurality of flow restrictors or regulators providing fluid communication between one of the plurality of reaction vessels and (i) the entrance control volume, or alternatively, (ii) the exit control volume, the flow restrictors or regulators being adapted such that maintaining a higher pressure in the entrance control volume than in the exit control volume results in fluid flow through the reaction vessels that is apportioned approximately equally between each of the plurality of reaction vessels.

15. The apparatus of claim 1, further comprising a sampling valve and a return line, the sampling valve providing selective fluid communication between the sampling probe and the return line, and between the sampling probe and the detector;
   wherein the return line vents fluid into the exit control volume.

16. The apparatus of claims 1, 2, 3, 4, 6, 7, 8, 9, 10, 11, 12, 13 or 14 wherein the flow restrictors are selected from the group consisting of capillary tubes, micromachined channels and pin holes.

17. The apparatus of claims 1, 2, 3, 6, 7, 8, 12, 13 or 14 further comprising an assembly for containing the vessels, the assembly comprising
   a base block having a planar top surface and a bottom surface, the top surface of the base block having a plurality of wells formed thereon, and
   a cover block having a planar bottom surface, the bottom surface of the cover block being disposed on the top surface of the base block, and the bottom surface of the cover block having a plurality of depressions formed thereon,
   the cover block being removably attached to the base block with each of the plurality of depressions being in substantial alignment with one of the wells, such that the aligned depressions and wells form cavities for containing the vessels.

18. The apparatus of claim 5, further comprising a pressure regulator in the entrance control volume.

19. The apparatus of claim 5 further comprising a pressure regulator in the exit control volume.

20. The apparatus of claim 5, wherein the fluid handling system further comprises a fluid distribution valve having a first valve portion and a second valve portion, and a plurality of exhaust conduits providing fluid communication between the fluid distribution valve and the exit control volume;
   wherein the first valve portion provides selective fluid communication between a test fluid source and the flow restrictors and between the test fluid source and the exhaust conduits;
   the second valve portion provides selective fluid communication between an insert fluid source and the flow restrictors and between the inert fluid source and the exhaust conduits; and
   the resistance to fluid flow in each of the exhaust conduits is approximately the same and is about equal to the resistance to fluid flow in each of the flow restrictors so that fluid flow is apportioned approximately equally between each of the vessels and exhaust conduits.

21. The apparatus of claim 5, further comprising:
a first metering tube and a second metering tube in fluid communication with the sampling valve, the first metering tube and the second metering tube having substantially the same volume, and the sampling valve adapted to switch between a first flow network and a second flow network;
wherein the first flow network provides fluid communication between the sample bypass, the first metering tube and the exit control volume, and between a carrier gas source, the second metering tube, and the detector;
the second flow network provides fluid communication between the sample bypass, the second metering tube and the exit control volume, and between the carrier gas source, the first metering tube, and the detector;
so that switching from the first flow network to the second flow network results in transport of sample fluid within the first metering tube to the detector, and switching from the second flow network to the first flow network results in transport of sample fluid within the second metering tube to the detector.

22. The apparatus of claim 21, wherein the overall resistance to fluid flow in each flow path between the vessel outlets and the exit control volume is approximately the same.

23. The apparatus of claim 5, wherein the flow restrictors are one of capillary tubes, micromachined channels, and pin holes.

24. The apparatus of claim 5, further comprising:
flow regulators located along flow paths between the flow restrictors and one of the entrance control volume, the exit control volume and the vessels.

25. The apparatus of claim 24, wherein each of the flow regulators comprise:
a flow sensor in communication with a flow controller;
wherein the flow sensor determines flow rate by detecting a temperature difference between sensor elements located upstream of the flow controller; and
the flow controller adjusts fluid flow rate in response to a signal from the flow sensor by changing fluid temperature in the flow path.

26. The apparatus of claim 5 further comprising a system for regulating temperature of each of the plurality of vessels.

27. The apparatus of claim 26, wherein the system for regulating temperature of each of the vessels comprises a heating element and a temperature sensor, the heating element and temperature sensor in thermal contact with the vessels and in communication with a processor;
wherein the processor adjusts the temperature of the vessels in response to a signal from the temperature sensor by changing heat output of the heating element.

28. The apparatus of claim 27, further comprising a plurality of elongated heating elements, wherein all of the elongated heating elements in thermal contact with a particular row of vessels are in approximate axial alignment and are about parallel to the particular row of vessels.

29. The apparatus of claim 5, wherein the detector is one of a gas chromatograph, a mass spectrometer, a visible spectrometer, an ultraviolet spectrometer, and an infrared spectrometer.

30. The apparatus of claim 5, further comprising an assembly for containing the vessels, the assembly comprised of:
a base block having a planar top surface, and a bottom surface, the top surface of the base block having a plurality of wells formed thereon; and
a cover block having a planar bottom surface, the bottom surface of the cover block disposed on the top surface of the base block, and the bottom surface of the cover block having a plurality of depressions formed thereon;
wherein the cover block is removably attached to the base block, and each of the depressions is in substantial alignment with one of the wells, such that the aligned depressions and wells form cavities for containing the vessels.

31. The apparatus of claim 30, wherein the assembly further comprises vessel inlet ports and vessel outlet ports located on the bottom surface of the base cover;
wherein each of the vessel inlet ports provides fluid communication with the inlet of only one of the vessels, and each of the vessel outlet ports provides fluid communication with the outlet of only one of the vessels.

32. The apparatus of claim 6, further comprising a sampling valve and a return line, the sampling valve providing selective fluid communication between the sampling probe and the return line, and between the sampling probe and the detector;
wherein the return line vents fluid into the exit control volume.

33. The apparatus of claim 7, further comprising:
a first metering tube and a second metering tube in fluid communication with the sampling valve, the first metering tube and the second metering tube having substantially the same volume, and the sampling valve adapted to switch between a first flow network and a second flow network;
wherein the first flow network provides fluid communication between the sample bypass, the first metering tube and the exit control volume, and between a carrier gas source, the second metering tube, and the detector;
the second flow network provides fluid communication between the sample bypass, the second metering tube and the exit control volume, and between the carrier gas source, the first metering tube, and the detector;
so that switching from the first flow network to the second flow network results in transport of sample fluid within the first metering tube to the detector, and switching from the second flow network to the first flow network results in transport of sample fluid within the second metering tube to the detector.

34. The apparatus of claim 33, wherein the overall resistance to fluid flow in each flow path between the vessel outlets and the exit control volume is approximately the same.

35. The apparatus of claim 12, further comprising a sampling valve and a return line, the sampling valve providing selective fluid communication between the sampling probe and the return line, and between the sampling probe and the detector, the return line venting fluid into the exit control volume.

36. The apparatus of claim 14 wherein the fluid handling system further comprises a plurality of exhaust conduits providing fluid communication between the fluid distribution valve and the exit control volume, wherein
the fluid distribution valve comprises a first valve portion and a second valve portion, the first valve portion providing selective fluid communication between a test fluid source and the flow restrictors or regulators and between the test fluid source and the exhaust conduits, the second valve portion providing selective fluid communication between an inert fluid source and the flow restrictors or regulators and between the inert fluid source and the exhaust conduits, the resistance to fluid flow in each of the plurality of exhaust conduits being approximately the same and being about equal to the resistance to fluid flow in each of the plurality of flow restrictors or regulators, so that fluid flow is apportioned approximately equally between each of the plurality of reaction vessels and plurality of exhaust conduits.

37. The apparatus of claim 14 wherein the fluid handling system further comprises a selection valve providing selective fluid communication between a selected reduction vessel and the detector such that a test fluid can be sequentially directed from the selected reaction vessel to the detector.

38. The apparatus of claim 14 wherein the fluid handling system further comprises a selection valve providing selective fluid communication between a selected reduction vessel and the detector, such that a test fluid can be sequentially directed from the selected reaction vessel to the detector, and a control system for synchronizing the fluid distribution valve and the selection valve such that a time interval between initial contact of the test fluid with a library member in a reaction vessel and analysis of reactor effluent is about the same for the plurality of reaction vessels.

39. The apparatus of claims 12, 13 or 14 wherein the fluid handling system comprises flow restrictors.

40. The apparatus of claims 12, 13 or 14 wherein each of the plurality of flow restrictors or regulators provides fluid communication between the entrance control volume and one of the plurality of reaction vessels.

41. The apparatus of claims 6, 7, 8, 9, 11 or 14 wherein the fluid handling system comprises flow restrictors, and each of the plurality of flow restrictors provides fluid communication between the entrance control volume and one of the plurality of reaction vessels.

42. The apparatus of claims 12, 13 or 14 wherein each of the plurality of flow restrictors or regulators provides fluid communication between one of the plurality of reaction vessels and the exit control volume.

43. The apparatus of claims 6, 7, 8, 9, 11, 12, 13 or 14 wherein the fluid handling system is a gas handling system for providing gaseous flow simultaneously through the plurality of reaction vessels.

44. The apparatus of claims 6, 7, 8, 9, 11, 12, 13 or 14 wherein the fluid handling system is a liquid handling system for providing liquid flow simultaneously through the plurality of reaction vessels.

45. The apparatus of claims 6, 7, 8, 9, 11, 12, 13 or 14 further comprising a system for regulating the temperature of each of the plurality of reaction vessels.

46. The apparatus of claims 1, 2, 3, 4, 10, 12, 13 or 14 wherein the detector is selected from the group consisting of a gas chromatograph, a mass spectrometer, a visible spectrometer, an ultraviolet spectrometer and an infrared spectrometer.

47. The apparatus of claim 5, 6, 7, 8, 9, 11, 12, 13 or 14 wherein the plurality of reaction vessels is at least six reaction vessels and the plurality of flow restrictors or regulators is at least six flow restrictors or regulators.

48. The apparatus of claims 1, 2, 3, 4, 5, 6, 7, 8, 9, 10, 11, 12, 13 or 14 wherein the plurality of reaction vessels is at least forty-eight vessels and the plurality of flow restrictors or regulators is at least forty-eight flow restrictors or regulators.

49. The apparatus of claims 6, 7, 8, 9, 11, 12, 13 or 14 further comprising a catalyst in each of the plurality of reaction vessels.

50. The apparatus of claims 1, 2, 3, 4, 5, 6, 7, 8, 9, 10, 11, 12, 13 or 14 wherein the plurality of reaction vessels is at least twelve reaction vessels and the plurality of flow restrictors or regulators is at least twelve flow restrictors or regulators.

* * * * *

UNITED STATES PATENT AND TRADEMARK OFFICE
CERTIFICATE OF CORRECTION

PATENT NO.    : 6,149,882
DATED         : November 21, 2000
INVENTOR(S)   : Guan et al.

It is certified that error appears in the above-identified patent and that said Letters Patent is hereby corrected as shown below:

Column 16,
Line 14, a comma should be inserted after the word "volume"

Column 18,
Line 65, the word -- reaction -- should be inserted between "sample" and "vessel"

Column 19,
Line 57, the word -- reaction -- should be inserted between "non-selected" and "vessels"

Column 20,
Line 26, the word "test" should be replaced with -- reactive --

Column 22,
Lines 31 and 40, the word -- reaction -- should be inserted between "of" and "vessels"

Column 23,
Line 8, the word "nlet" should be replaced with -- inlet --
Line 35, the word -- reaction -- should be inserted between "selected" and "vessels"
Line 36, the word -- reaction -- should be inserted between "non-selected" and "vessels"

Column 28,
Line 20, the word "claim" should be replaced with -- claims --

Signed and Sealed this

Seventeenth Day of June, 2003

JAMES E. ROGAN
*Director of the United States Patent and Trademark Office*